United States Patent [19]
Skubitz et al.

[11] Patent Number: 5,851,226
[45] Date of Patent: Dec. 22, 1998

[54] TEMPORARY TRANSVENOUS ENDOCARDIAL LEAD

[75] Inventors: Frank L. Skubitz, Andover; Gerald M. Herman, Fridley; Terrell M. Williams, Brooklyn Park, all of Minn.

[73] Assignee: Medtronic, Inc.

[21] Appl. No.: 734,915

[22] Filed: Oct. 22, 1996

[51] Int. Cl.⁶ .................................................. A61N 1/36
[52] U.S. Cl. .......................................... 607/126; 607/127
[58] Field of Search .................................. 607/126–128, 607/130–132; 600/375

[56] References Cited

U.S. PATENT DOCUMENTS

| | | |
|---|---|---|
| 3,737,579 | 6/1973 | Bolduc . |
| 3,769,984 | 11/1973 | Muench . |
| 3,815,611 | 6/1974 | Denniston, III . |
| 3,827,428 | 8/1974 | Hon et al. . |
| 3,844,292 | 10/1974 | Bolduc ..................................... 607/126 |
| 3,893,461 | 7/1975 | Preston . |
| 3,903,896 | 9/1975 | Harmjanz . |
| 3,915,174 | 10/1975 | Preston . |
| 4,010,755 | 3/1977 | Preston . |
| 4,103,690 | 8/1978 | Harris . |
| 4,106,512 | 8/1978 | Bisping . |
| 4,112,952 | 9/1978 | Thomas et al. . |
| 4,135,518 | 1/1979 | Dutcher . |
| 4,180,080 | 12/1979 | Murphy . |
| 4,214,594 | 7/1980 | Little . |
| 4,233,992 | 11/1980 | Bisping . |
| 4,271,847 | 6/1981 | Stokes . |
| 4,280,512 | 7/1981 | Karr et al. . |
| 4,282,885 | 8/1981 | Bisping . |
| 4,289,138 | 9/1981 | Halvorsen . |
| 4,475,560 | 10/1984 | Tarjan et al. . |
| 4,544,078 | 10/1985 | Arenas et al. . |
| 4,602,645 | 7/1986 | Barrington et al. . |
| 4,699,157 | 10/1987 | Shonk . |
| 4,762,136 | 8/1988 | Baker, Jr. . |
| 4,799,499 | 1/1989 | Bisping . |
| 4,819,661 | 4/1989 | Heil, Jr. et al. . |
| 4,886,074 | 12/1989 | Bisping . |
| 5,009,839 | 4/1991 | Miyata et al. . |
| 5,246,014 | 9/1993 | Williams et al. ....................... 607/122 |
| 5,259,394 | 11/1993 | Bens ........................................ 607/127 |
| 5,261,417 | 11/1993 | Osypka ................................... 607/127 |
| 5,261,419 | 11/1993 | Osypka ................................... 607/122 |
| 5,314,462 | 5/1994 | Heil, Jr. et al. ......................... 607/128 |
| 5,356,427 | 10/1994 | Miyata et al. .......................... 607/122 |
| 5,374,287 | 12/1994 | Rubin ..................................... 607/131 |
| 5,545,201 | 8/1996 | Helland et al. ......................... 607/127 |

OTHER PUBLICATIONS

Brochure: *Medtronic ®Temptron™ Temporary Disposable Bipolar Leads*, Medtronic, Inc., Mar. 1982.

Brochure: *USCI® Bipolar Temporary Transvenous Pacing Electrode*, C. R. Bard, Inc., Jun. 1994.

Brochure: *ProCath® Temporary Pacing Catheter*, ProCath Corporation, Sep. 1994.

Brochure: *Ky U–Peel—Instructions for Implantation*, Oscor Medical Corporation, Nov. 1986.

Togawa et al., "Experimental and clinical evaluation of a screw–in electrode", Conference Proceedings of the 5th International Symposium on Cardiac Pacing, Mar. 1976.

*Primary Examiner*—William E. Kamm
*Assistant Examiner*—George R. Evanisko
*Attorney, Agent, or Firm*—Thomas F. Woods; Harold R. Patton

[57] ABSTRACT

A novel low cost, temporary pacing lead that provides superior torque transfer characteristics and positive affixation to the endocardial wall. The lead system of the present invention provides up to ten times more torque transmission between its proximal and distal ends than may be attained using prior art temporary leads. Additionally, the lead body of the present invention has a ratio of ring electrode surface area to tip electrode surface area that exceeds about 2, and a tip electrode surface area less than or equal to 10 millimeters squared.

123 Claims, 14 Drawing Sheets

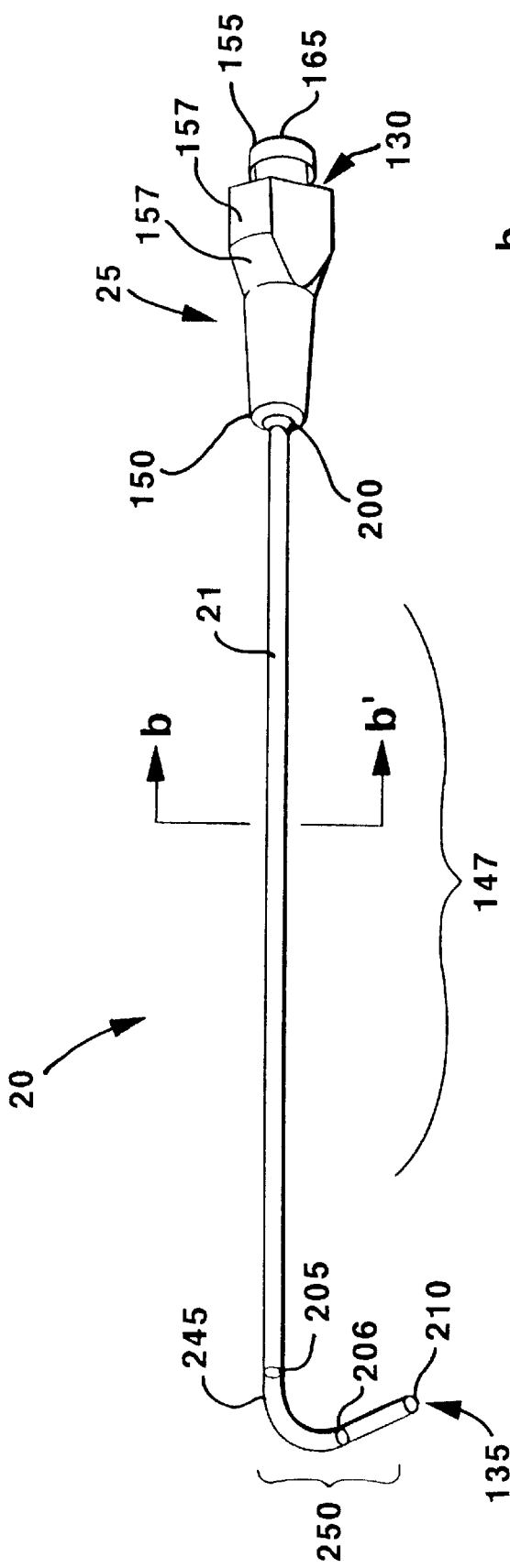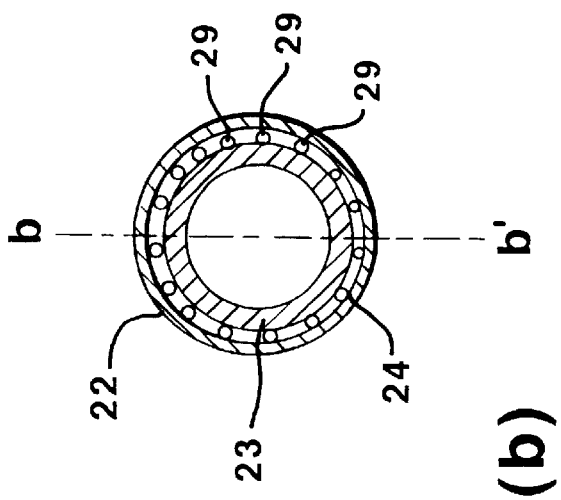
FIG.10(a)
FIG.10(b)

TEMPORARY TRANSVENOUS ENDOCARDIAL LEAD

FIELD OF THE INVENTION

The present invention relates generally to implantable pacing leads, and more particularly to temporary transvenous endocardial leads for pacing or other medical applications.

BACKGROUND OF THE INVENTION

Endocardial pacing leads may be classified in two broad categories: permanent pacing leads and temporary pacing leads. Permanent and temporary pacing leads are generally characterized in having different physical structures, materials and configurations. Structural differences between the two general types of pacing leads are driven primarily by cost considerations and the different natures of the applications for which the two types of leads are employed. In 1996 U.S. dollars many temporary pacing leads have actual or suggested retail prices in the U.S. that vary between about $75 and $200. In contrast, many permanent pacing leads sold in the U.S. have actual or suggested retail prices exceeding $1,000. Most temporary pacing leads are used for one week or less and then disposed of, while permanent pacing leads often remain implanted and functioning in patients for five years or longer.

When a permanent pacing lead is implanted in a patient, a pacemaker and an electrical connection between the pacing lead and the pacemaker are generally embedded within the body. Permanent pacing leads are commonly implanted with the aid of stylets that increase the speed and accuracy of lead electrode placement. Moreover, once the lead has been implanted and the stylet withdrawn, the remaining lead body becomes flexible and does not retain the stiffness imparted by the stylet. Thus, stylets are highly desirable and often used in permanent leads.

When implanting a permanent pacing lead, a peripheral vein such as the left or right subclavian vein is punctured by an introducer through an incised portion of the skin. A prior art "catheter" or a lead containing a stylet is inserted through the introducer. When a prior art "catheter" is used, the "catheter's" distal end is held at the apex of the right ventricle or right atrium while a temporary lead is inserted through the prior art "catheter" until the distal end of the lead engages and is lodged or otherwise affixed to the endocardium of the right ventricle or right atrium; the prior art "catheter" is then withdrawn. If a lead having a stylet is used, the distal end of the lead is guided to the apex of the right ventricle or the atrial appendage in the atrium, the lead electrode tip is affixed to the endocardium and the stylet is removed.

We use the term "catheter" above respecting the prior art because prior art catheters were generally tubes formed from rubber, neoprene or plastic tubes that had no inner braiding or other structural strengthening means that permitted the control or transfer of torque. Thus, the term "catheter," as it applies to the prior art discussed here, does not include within its scope "guide catheters" of the present invention that, contrariwise, do permit the transfer and control of torque from their proximal to distal ends.

It is notable that no permanent leads known to the inventors of the present invention have employed catheters for several decades. The are several reasons why such prior art catheters are no longer used. Prior art catheters could not provide as much torque control or transmission as stylets. The thick sidewalls and correspondingly large diameter of prior art catheters rendered such catheters large in diameter. In fact, many such catheters had such large diameters that they could not be inserted in the cephalic veins of a significant number of patients.

Temporary transvenous endocardial pacing leads are generally used prior to pacemaker implant surgery or in emergency treatment of heart arrythmias and myocardial infarction. In temporary pacing, the distal end of a temporary pacing lead is inserted transvenously in the body using some of the techniques described above for permanent leads while the proximal end is located outside the body where electrical and mechanical connections to an external temporary pacemaker are made. The positive and negative connectors at the proximal end of the temporary lead are connected to the terminals of the temporary pacemaker or patient cable provided for strain relief or extension purposes. (A patient cable is usually, in turn, then connected to a temporary pacemaker.) The temporary pacemaker provides pulses of electrical energy to stimulate the endocardium through the temporary pacing lead. The stimulation rate, output amplitude and sensitivity of the temporary pacemaker are then adjusted. Typically, a temporary pacing lead is extricated and withdrawn from a patient when a permanent, implantable pacemaker and corresponding permanent lead are implanted, or when the need for pacing no longer exists.

Epicardial pacing leads are often used in temporary pacing applications following transthoracic surgery, where the electrode is affixed to the surface of the heart. It is an advantage of endocardial leads that they typically require lower stimulation thresholds to pace the heart than those required with epicardial leads because endocardial leads provide lower stimulation thresholds over time. Temporary pacing leads should not be reused, are designed to be disposed of after a single use, and are not designed for use over prolonged periods of time.

While low cost temporary pacing leads have been widely used for decades, low cost temporary leads known heretofore have never been used in conjunction with stylets or guide catheters. This may be because stylets and guide catheters add considerable, excessive and therefore unaffordable cost to known temporary pacing lead products, or simply because heretofore no one has previously conceived of combining temporary pacing leads and guide catheters or stylets.

Prior art low cost temporary pacing leads have never included active fixation structures at their distal ends for attaching the lead to the endocardium, despite the clear advantages and benefits of such devices. Among other reasons, cost considerations have prevented the use of active fixation devices in temporary pacing leads. Active fixation devices generally require expensive sheathing or shrouding structures to protect venous and cardiac tissue from the device during implantation. Such sheathing structures include those retracted to expose the device when the distal end of the lead is positioned at the affixation site, as well as glycol-containing compounds disposed about the active fixation device that slowly dissolve upon being immersed in a warm, sanguine medium. Examples of mechanical sheathing structures for transvenous pacing leads include various distal end sheaths and helical electrodes retractable by stylet means.

Temporary pacing leads known in the prior art fall into two broad categories: (1) coaxial temporary pacing leads, and (2) temporary pacing leads having one, two or three lumens.

Coaxial temporary pacing leads are characterized in having inner and outer conductors separated by an electrically insulative material, where the inner conductor typically comprises three twisted or stranded wires, and the outer conductor typically comprises a woven metallic mesh formed of 16 woven wires. The outermost layer is electrically insulative and is typically formed of urethane, polyurethane or polyethylene. Coaxial temporary leads are usually 6 to 7 French in diameter, but may be as small as 4 French in diameter. Examples of coaxial temporary pacing leads include MEDTRONIC® Model Numbers 6704, 6704A, 6705 and 6705A TEMPTRON® leads described in MEDTRONIC publication reference number MC 78-PE-0086c 179562-001, the disclosure of which is hereby incorporated by reference in its entirety. FIG. 1 shows a side cutaway view of a prior art coaxial temporary lead. FIG. 2(a) shows a cross-sectional view of the lead of FIG. 1.

Single, double or tri-lumen temporary pacing leads are characterized in having one, two or three lumens for housing two or more electrical conductors. The conductors are usually electrically insulated from one another by their respective layers of electrical insulation or by lead body electrical insulation. Each conductor typically comprises up to 8 twisted or braided wires disposed within the insulation. Examples of single and double lumen temporary pacing leads include DAIG™ temporary pacing lead model numbers 401674, 401675, 401665 and 410666, USCI™ temporary pacing lead model numbers 7153, 7151, 7157, 8154, 7150, 8153, 6221, 7406 and 6222, TELECTRONICS CORDIS™ temporary pacing lead model numbers 370-230, 370-132, 370-330, 370-136 and 370-420, and ELECATH™ temporary pacing lead model numbers 11-KSS5, 11-KSS6, 11-KSS4, 22-0865 and 22-0866. PROCATH CORPORATION™ of Berlin, N.J. also manufactures single lumen temporary pacing leads. FIG. 2(b) shows the cross-sectional structure of a prior art single lumen temporary lead having two electrical conductors disposed side by side. FIG. 2(c) shows the cross-sectional structure of a prior art tri-lumen temporary lead having three separate conductors.

Some ideal attributes of a temporary pacing lead include: (1) small lead diameter; (2) secure placement of the tip electrode in the selected heart chamber; (3) high degree of steerability, control and torque transfer during implantation; (4) minimal damage to vein, heart valve and endocardial tissue during implantation; (5) reliable conduction of electrical impulses during use; (6) easy removal from the heart chamber with minimum tissue damage, and (7) low cost.

Small diameter leads are desirable for several reasons. A vein has a finite diameter and thus a finite cross-sectional area for receiving one or more leads. A small diameter temporary lead is accommodated more readily in, and impedes less the flow of blood through, a vein than does a large diameter temporary lead. A small diameter lead also provides minimum interference with the flow of blood through a venous vessel or a heart valve. Large diameter leads are known to adversely affect heart valve operation. Finally, some patients already have at least one implanted lead when an additional temporary pacing lead must be implanted; having a small diameter lead becomes a significant advantage under such circumstances.

Large diameter temporary leads are more likely to rub against and dislodge permanently implanted leads during lead removal than are small diameter temporary leads. Large diameter temporary leads present a greater mass of foreign material to the body, and thus present a higher risk of occlusive thrombosis, scar tissue formation and thrombotic pulmonary embolism than do small diameter temporary leads. Because large diameter leads are generally stiff, they more likely to perforate veins or cardiac tissue, are more prone to lead fatigue and subsequent failure, and may take a long time to place. A primary cause of lead failure is the crushing of large diameter lead bodies between the relatively small space between the clavical and first rib.

Despite the numerous advantages of small diameter leads described above, in practice small diameter leads have proved difficult to manufacture, and are frequently unreliable and difficult to place. For example, many prior art small diameter leads are too pliable to permit sufficient steerability and control for accurate lead placement. Additionally, the high degree of flexibility and limpness characterizing many small diameter leads may lead to excessive time and effort being required for lead placement. In consequence, the cost for the procedure rises and the patient is progressively exposed to more risk factors as the amount of time expended to complete the procedure increases. Finally, most small diameter leads do not transfer sufficient torque between the proximal and distal ends to permit the tip electrode to be affixed to cardiac tissue at a selected site with any degree of accuracy.

Secure placement of the tip electrode in the selected heart chamber is required to assure appropriate and reliable depolarization or "capture" of cardiac tissue by electrical stimuli delivered by the temporary pacemaker. Known temporary transvenous leads suffer from a relatively high rate of dislodgment from sites adjacent or on the endocardium. This is not surprising in view of the fact that no prior art temporary transvenous pacing leads utilize active fixation devices to positively secure the electrode tip to the endocardium. Instead, known temporary pacing leads rely on force provided by a bent or curved lead body as a means of pushing the distal electrode tip against endocardial tissue. If the pacing lead body or tip shifts position as a result, for example, of patient postural changes, the tip electrode may disengage or float away from the endocardium. This, in turn, may result in a loss of capture, or in a reduction of the degree of electrical coupling between the electrode and endocardium.

Treadmill tests can yield valuable information concerning a patient's health and diagnosis that may not be obtained in any other way. Despite their clear benefits, however, physicians rarely prescribe treadmill tests for patients having implanted temporary transvenous pacing leads because temporary pacing leads typically become dislodged easily when patients are ambulatory or otherwise move about. Furthermore, it is common that patients having implanted temporary pacing leads cannot be paced in the DDD mode because at least one of the leads dislodges or becomes poorly coupled electrically to the endocardium after the lead implantation procedure has been completed. This is because it is very difficult to maintain pacing in the atrium over any appreciable length of time when the pacing lead has no means for fixation to the atrial wall.

It is desirable that temporary pacing leads have a high degree of steerability, control and torque transfer to permit relatively quick and accurate placement of the electrode tip at the desired site within the heart, and the initiation of temporary pacing with minimum delay and tissue trauma. Speed and accuracy of lead placement become especially important when attempting to restore a patient's heartbeat under emergency conditions. In the past, there have been a limited number of sites in the atrium and ventricle where lead placement could be effected. The accuracy of where the pacing lead is placed in the atrium or ventricle thus assumes considerable importance.

There are two known means of achieving a high degree of permanent lead steerability and control: (1) placing a stylet in a lumen inside the lead body, and (2) using a guide catheter in conjunction with the lead. Stylets and guide catheters, however, impart significant additional and unaffordable cost to temporary pacing leads, and as a result are not employed in known temporary pacing leads.

Physicians often rely on the tactile feedback and "feel" provided by the lead during implantation for accurate and quick placement. Because of their limpness and excessive flexibility, known small diameter pacing leads typically provide virtually no tactile feedback or "feel" to physicians. Small diameter pacing leads are also notoriously poor at transferring torque between their proximal and distal ends. As a result of the foregoing factors, known small diameter pacing leads generally prove difficult to accurately and quickly place.

Contrariwise, and owing to their stiffness, known large diameter pacing leads often provide a high degree of tactile feedback and "feel." Unfortunately, large diameter pacing leads typically lack sensitivity in the feedback and "feel" they provide. Thus, while known large diameter pacing leads often provide good torque transfer and a high degree of tactile feedback, typically they are also incapable of providing the sensitivity required for a physician to discriminate between endocardial tissue and venous tissue. Consequently, the risk of inadvertently perforating venous or cardiac tissue is made greater with known large diameter pacing leads. Additionally, and owing to their stiffness, large diameter leads exert forces on tip electrodes which promote the growth of scar tissue which, in turn, increases pacing thresholds.

Ideally, temporary pacing leads should cause no damage to vein, heart valve and cardiac tissue during implantation. The temporary lead should have a highly flexible and soft distal tip that readily follows the direction of venous blood flow. Such directional following is often referred to as "floating" the lead or catheter through the venous system. A soft flexible distal tip on the lead or catheter may help prevent trauma to the surrounding venous and cardiac tissues as the lead is directed to the fixation site.

Temporary pacing leads should reliably conduct electrical pulses from the pacemaker even when sutures at the lead anchor suture site are drawn too tight, the lead is stressed by excessive patient movement, or when the pacemaker or attached lead is subjected to rough handling by hospital personnel. Temporary pacing leads are designed for a single use over a limited duration of time, and therefore are typically not constructed of materials that are as biostable, durable, strong or robust as those used in permanent pacing leads. Thus, known temporary pacing leads tend to fail more frequently than permanent pacing leads. Many failures of known temporary pacing leads are caused by fatigue and breaking of electrical conductor wires, electrical insulation that cracks or splits, or electrodes that become pitted or corroded.

When the need for temporary pacing no longer exists, the distal end of the temporary pacing lead should ideally be easily removable from heart chamber. Some known temporary pacing leads suffer from the disadvantage of occasionally damaging heart tissue upon being extracted from the tribiculae in which they are lodged. Other known temporary pacing leads having curved or J-shaped ends for pushing the tip electrode against the endocardium occasionally prove difficult to remove from the heart without at least some tissue trauma occurring.

Finally, temporary pacing leads should be available at low cost, especially since they are used only one time, and then for a very limited duration of time. Heretofore, providing a temporary pacing lead at low cost that has all or most of the foregoing desired attributes has proved impossible, despite the obvious and clear motivations for doing so.

Not surprisingly, no temporary pacing lead known in the prior art has most or all of the above-enumerated desirable safety, performance and cost attributes. What is needed is a low cost, yet still safe, reliable, small diameter, highly steerable, easily removable temporary transvenous endocardial pacing lead capable of reliably capturing, pacing and sensing the heart while causing minimum trauma to heart tissue during implantation and removal.

Transvenous endocardial leads and fetal scalp electrodes are well known in the art, some examples of which may be found in the issued U.S. Patents listed in Table 1 below.

TABLE 1

| | Prior Art Patents | |
|---|---|---|
| U.S. Pat. No. | Inventor(s) | Issue Date |
| 3,348,548 | Chardack | 24 Oct. 1967 |
| 3,737,579 | Bolduc | 5 June 1973 |
| 3,769,984 | Muench | 6 Nov. 1973 |
| 3,815,611 | Denniston, III | 11 June 1974 |
| 3,827,428 | Hon et al. | 6 Aug. 1974 |
| 3,893,461 | Preston | 8 July 1975 |
| 3,903,896 | Hamjanz | 9 Sept. 1975 |
| 3,915,174 | Preston | 28 Oct. 1975 |
| 4,010,755 | Preston | 8 March 1977 |
| 4,106,512 | Bisping | 15 Aug. 1978 |
| 4,112,952 | Thomas et al. | 12 Sept. 1978 |
| 4,180,080 | Murphy | 25 Dec. 1979 |
| 4,214,594 | Little | 29 Jul. 1980 |
| 4,233,992 | Bisping | 18 Nov. 1980 |
| 4,271,847 | Stokes | 9 June 1981 |
| 4,280,512 | Karr et al. | 28 Jul. 1981 |
| 4,282,885 | Bisping | 11 Aug. 1981 |
| 4,475,560 | Tarjan et al. | 9 Oct. 1984 |
| 4,602,645 | Barrington et al. | 29 July 1986 |
| 4,699,157 | Shonk | 13 Oct. 1987 |
| 4,762,136 | Baker, Jr. | 9 Aug. 1988 |
| 4,799,499 | Bisping | 24 Jan. 1989 |
| 4,819,661 | Heil, Jr. et al. | 11 April 1989 |
| 4,886,074 | Bisping | 12 Dec. 989 |
| 5,099,839 | Miyata et al. | 31 March 1992 |
| 5,246,014 | Williams et al. | 21 Sept. 1993 |
| 5,261,417 | Osypka | 16 Nov. 1993 |
| 5,261,419 | Osypka | 16 Nov. 1993 |
| 5,314,462 | Heil, Jr. et al. | 24 May 1994 |
| 5,356,427 | Miyata et al. | 18 Oct. 1994 |

All patents listed in Table 1 hereinabove are hereby incorporated by reference herein in their respective entireties. As those of ordinary skill in the art will appreciate readily upon reading the Summary of the Invention, Detailed Description of the Preferred Embodiments and claims set forth below, many of the devices and methods disclosed in the patents of Table 1 may be modified advantageously by using the teachings of the present invention.

SUMMARY OF THE INVENTION

The present invention has certain objects. That is, the present invention provides solutions to many problems existing in the prior art respecting temporary pacing or sensing leads. Those problems include: (a) poor transfer of torque from one end of the lead to the other; (b) high rates of lead dislodgment; (c) an inability to pace ambulatory patients; (d) perforation of the heart or venous tissue; (e) lack of steerability or control during implantation; (f) inaccurate electrode placement; (g) poor electrode affixation or coupling to the heart wall; (h) unreliable pacing of the atrium; (i) an inability to select and pace alternate intracardiac sites to provide better cardiac output or better capture when the first selected site is infarcted, ishemic or necrotic, and (j) poor sensing of atrial and ventricular events. No known prior art temporary pacing leads provide any means of actively affixing the tip electrode to the heart wall. Finally, the use of large diameter prior art temporary leads occasionally caused pulmonary embolism when such temporary leads were implanted adjacent to other large diameter permanent or temporary leads and blood stagnation occurred between the lead bodies.

The present invention has the object of solving at least some of the foregoing problems. While some permanent leads are capable of solving at least some of the foregoing problems, they are rarely employed in temporary applications because of their prohibitively high cost. It is therefore another object of the present invention to provide an improved temporary pacing lead that may be manufactured and sold at low cost, yet still fulfill many or even most of the other foregoing objects.

In comparison to known temporary leads, the present invention provides numerous advantages that include: (a) increasing the ratio of the ring electrode surface area to the tip electrode surface area to 2:1 and beyond to permit improved sensing of intra-cardiac events; (b) decreasing the surface area of the tip electrode to 10 square millimeters or less, thus permitting the delivery of higher current densities to heart tissue and resulting in lower thresholds for pacing; (c) permitting reliable pacing of the atrium owing to its positive affixation feature; (d) permitting more precise placement of electrodes to enable, for example, physiologically more appropriate stimulation than has heretofore been possible (the tip electrode, for example, may be placed in close proximity to the Bundle of His); (e) providing more pacing site options to physicians; (f) better, more reliable, electrode affixation to the heart wall; (g) providing nested or staggered lead connections at its proximal ends so that no bifurcated connector assembly is required for connection to patient cables or EPGs; (h) eliminating the requirement for ring-to-tip support tubing; (i) improving torque transmission between the proximal and distal ends; (j) reducing the risk of perforating venous or cardiac tissue during lead implantation; (k) preventing "worm-holing" of the active fixation tip electrode into the myocardium when the lead body is rotated through more revolutions than the helical coil is designed to accommodate; (l) reducing the risk of imparting trauma to cardiac or venous tissue upon lead removal; (m) reducing the rate at which temporary leads dislodge from cardiac tissue; (n) reducing the number and magnitude of risk factors to which patients may be exposed in post-operative follow-up surgical procedures for re-implanting dislodged leads; (o) reducing overall surgery and implantation costs; (p) permitting reliable, uninterrupted treadmill or other exercise tests to be performed on patients having temporary pacing leads implanted within them; (q) reliably conducting electrical impulses from an EPG or an IPG to a desired cardiac site; (r) temporarily and reliably pacing patients in the DDD mode because two leads of the present invention may be implanted simultaneously, unlike prior art temporary leads, where generally only one such lead may be implanted; (s) impeding blood flow less; (t) reducing the occurrence of blood stagnation between large lead bodies; (u) interfering less with heart valve operation; (v) providing superior electrical coupling of the lead to cardiac tissue; (w) permitting a wider range of diagnostic tests to be employed; (x) providing improved tactile feedback and "feel" during lead implantation and extraction; (y) permitting more flexibility and choice in where the electrode may be placed, and (z) reducing the occurrence of lead body crushing between the clavical and first rib.

The temporary lead of the present invention forms a lead system comprising a lead body and a guide catheter, where the lead body and guide catheter function and cooperate together to provide a lead body that can be delivered accurately to a selected endocardial site, and then positively affixed thereto.

Some embodiments of the invention have certain features, including: (a) a temporary lead system comprising, in combination, a guide catheter and a lead body, the guide catheter providing a load or bearing surface against which the lead body acts when torque is transmitted between its proximal and distal ends; (b) a guide catheter that preferably slidingly, or otherwise, accepts a separate lead body therewithin, the distal end of the guide catheter being manually retractable to expose an active fixation device attached to the distal end of the lead body; (c) a guide catheter having an outer diameter of about 6 French or less; (d) a guide catheter having an inner diameter of about 4 French or less; (e) a guide catheter for a lead body having an outer diameter of about 4 French or less, wherein the outer surface of the otherwise substantially non-torqueable lead body engages the inner surface of the guide catheter such that the inner surface laterally restrains the lead body and acts as a load or bearing surface upon which axial forces imparted to the lead body by the physician act, thereby permitting the transfer of torque through the lead body from its proximal to distal ends; (f) a guide catheter having braided wires disposed therein; (g) a coaxial conductor having inner and outer conductors; (h) a lumen design having three or four conductors; (i) an outer conductor formed of 9–32 braided or twisted wires; (j) an inner conductor formed of 1–5 braided or twisted wires; (k) a lead body having an outer diameter of about French or less, and most preferably about 3.5 French or less; (l) a helical coil or other active fixation device attached to the distal end of the lead body; (m) a ratio of ring surface area to tip electrode surface area exceeding 2:1, and preferably exceeding 4:1; (n) a tip electrode having a surface area less than 10 square millimeters, and preferably less than 5 square millimeters; (o) staggered, nested, or bifurcated proximal end connectors, and (p) a lead construction that resists flex fatigue through the combination of small lead body diameter and small individual wire diameters.

Those of ordinary skill in the art will understand immediately upon referring to the drawings, detailed description of the preferred embodiments and claims hereof that many objects, features and advantages of the present invention will find application in the field of permanent pacing leads.

BRIEF DESCRIPTION OF THE DRAWINGS

FIG. 10(*a*) shows a left perspective view of one embodiment of the guide catheter and proximal hub of the present invention;

FIG. 10(*b*) shows a cross-sectional view of the guide catheter shown in FIG. 10(*a*) and taken along line b–b'.

DETAILED DESCRIPTION OF THE PREFERRED EMBODIMENTS

Figure 1:
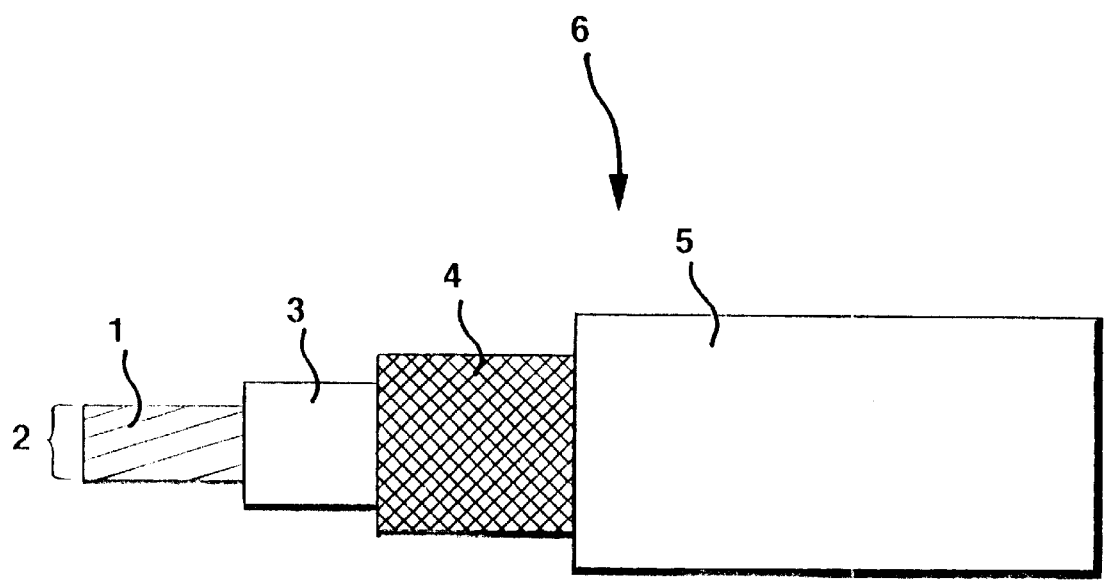
FIG. 1 shows a side cutaway view of a prior art coaxial temporary pacing lead.

As used in the specification and claims hereof, the following terms have the particular meanings and definitions set forth below.

The terms "temporary pacing lead" and "temporary lead" mean a low cost, implantable, percutaneously introduced, transvenous, endocardial lead having at least one electrode for pacing, capturing, cardioverting or defibrillating the heart at or near an endocardial site, the lead being intended for use over a relatively short and limited period of time that is usually several days in length and occasionally as long as about one month, the lead being disposed of after a single use, where the design and structure of, and materials used in, the lead correspond to the foregoing single use and low cost requirements. The terms "temporary pacing lead" and "temporary lead" include within their scopes unipolar and bipolar temporary pacing leads. The term "temporary pacing lead" does not include within its scope transvenous catheters or leads for ablating portions of the endocardium.

The term "low cost" means an operative, complete temporary pacing lead comprising a lead body, at least one electrical conductor disposed therewithin, an electrical connector attached to the proximal end of the at least one electrical conductor, and at least one electrode disposed at or near the distal end of the lead body, where the lead has a suggested or actual retail price in the United States and in 1996 U.S. dollars (or equivalent in foreign currency) that does not exceed $200.00

The term French means a unit of measurement, where 0.013 inches (thirteen thousandths of an inch) equals 1 (one) French.

The term "large diameter pacing lead" means a lead where the lead body has an outer, maximum diameter greater than about 6 French.

The term "active fixation" means the positive fixation of the distal end of a pacing lead, or a portion near the distal end of the pacing lead, to endocardial tissue, or through, propinquant to, or into endocardial tissue.

The term "braided" means the interweaving together of individual strands or electrical conductors.

The term "stranded" means the twisting together of individual strands or electrical conductors.

The term "twisted" means the entwining, twisting or twining together of individual strands or electrical wires.

The term "proximal" means that portion of an apparatus, or component or element of an apparatus, which is disposed in closer proximity to the end of the lead or guide catheter that remains outside a patient's body during a lead implantation procedure than it is to the end of the lead or guide catheter that is inserted first inside the patient's body during the lead implantation procedure.

The term "distal" means that portion of an apparatus, or component or element of an apparatus, which is disposed in closer proximity to the end of the lead or guide catheter that is inserted first inside a patient's body during a lead implantation procedure than it is to the end of the lead or guide catheter that remains outside the patient's body during the lead implantation procedure.

The term "guide catheter" means a catheter that is designed for use in combination or in conjunction with a separate lead body, where the guide catheter forms a tubular shape and accepts the lead body inside a central lumen or tube defined by inner sidewalls, the inner sidewalls providing a bearing or load surface against which the lead body acts when one lead body end is being rotated by a physician.

FIG. 1 shows a side cutaway view of a prior art coaxial temporary pacing lead similar to the TEMPTRON Model No. 6704 straight bipolar temporary pacing lead. The 6704 lead is implanted without the use of a stylet or a guide catheter, and has no active fixation mechanism disposed at the distal end thereof. Additionally, the 6704 lead requires a special adapter to be connected to its proximal end after implantation, where the adapter converts the in-line electrodes of the lead to bifurcated electrodes. Those bifurcated electrodes may then be attached mechanically and electrically to an EPG.

Figure 2A:
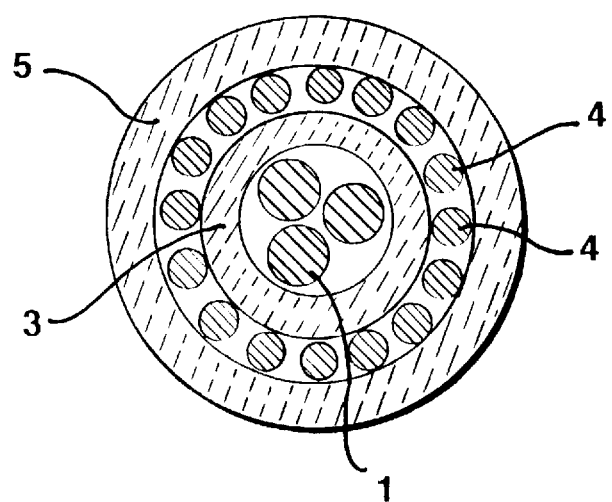
FIG. 2(a) shows a cross-sectional view of the lead of FIG. 1.

FIG. 2(*a*) shows a cross-sectional view of the prior art lead of FIG. 1. Wire 1 is one of several twisted or stranded wires that collectively form inner conductor 2. Typically, inner conductor 2 comprises 3 twisted stainless steel wires. At its distal end inner conductor 2 is typically connected mechanically and electrically to one of the pacing electrodes of the temporary pacing lead. At its proximal end inner conductor 2 is connected mechanically and electrically to a first pin connector.

Outer conductor 4 is separated from inner conductor 2 by insulative layer 3, where insulative layer 3 electrically insulates the two conductors from one another. Outer conductor 4 generally comprises about 16 electrically conductive stainless steel wires woven into a mesh, where 8 wires are woven in a first direction and 8 wires are woven in a second direction oblique to the first direction. Outer conductor 4 connects one of the pacing electrodes of the temporary pacing lead to a second pin connector. Outer insulative layer 5 is formed of biocompatible material such as polyurethane or a suitable silastic compound, and protects elements 1, 2, 3 and 4 of lead 6 from blood, oxygen, tissue and like substances found within the body.

When temporary pacing lead 6 is implanted transvenously, no guide catheter or stylet is used. Nor does temporary pacing lead 6 have any type of active fixation device attached to its distal end. Instead, the distal end of the lead is typically guided by fluoroscopic means into the right ventricle, where the tip of the lead is pushed into the trabeculae carnae located in the apex of the right ventricle. When the procedure succeeds, the tip lodges in the trabeculae carnae and remains positioned there. Alternatively, the distal end of the lead may be shaped by the implanting physician to form an arched or curved portion before the lead is implanted. After the lead has been implanted, and the distal end thereof has been positioned successfully in the ventricle, the arched or curved portion acts like a spring and biases the distal end of the lead against the endocardium and holds the tip electrode in contact with endocardial tissue.

Figure 2C:
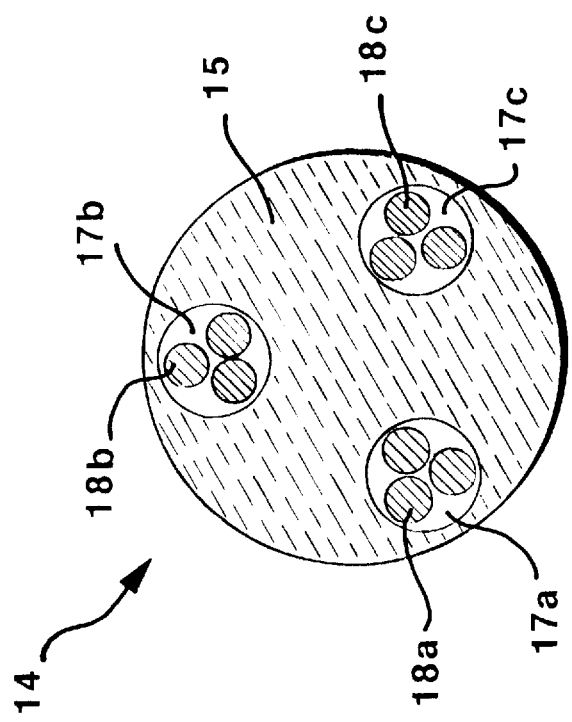
FIG. 2(c) shows a cross-sectional view of a prior art tri-lumen temporary pacing lead.
Figure 2B:
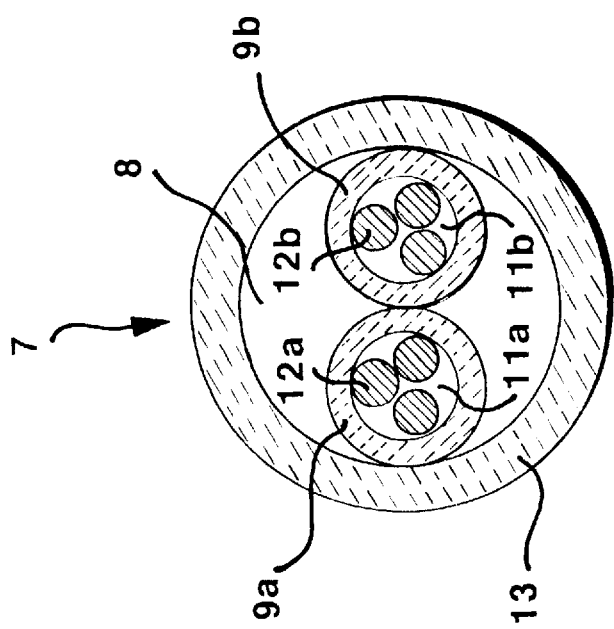
FIG. 2(b) shows a cross-sectional view of a prior art single lumen temporary pacing lead.

FIGS. 2(b) and 2(c) show cross-sectional views of prior art temporary pacing leads having one and three lumens, respectively. In FIG. 2(b), temporary lead 7 has first and second conductors 11(a) and 11(b), each of which generally comprises three twisted or stranded wires 12(a) or 12(b) encased in electrically insulative jacket or layer 9(a) or 9(b). Alternatively, only one of electrically insulative layers 9(a) and 9(b) is present in some prior art leads designs. Void 8 may or may not be filled with compressible material or the like. Outer jacket 13 is formed of biocompatible material and protects and sheaths the first and second conductors. The first and second conductors are electrically and mechanically connected to different electrodes and pin connectors at their distal and proximal ends, respectively.

In FIG. 2(c), temporary lead 14 has first, second and third conductors 17(a), 17(b) and 17(c), each of which generally comprises three twisted or stranded wires 18(a),18(b) and 18(c). The three conductors are surrounded by and encased in sheath 15 formed of biocompatible material. The first, second and third conductors are electrically and mechanically connected to different electrodes and pin connectors at their distal and proximal ends, respectively.

The temporary pacing leads shown in FIGS. 2(b) and 2(c) are implanted using the same techniques described above concerning the temporary pacing lead of FIG. 1. Furthermore, and also like the temporary pacing lead of FIG. 1, no guide catheter, stylet or active fixation device is used or forms part of either temporary pacing lead shown in FIG. 2(b) or 2(c). Like the lead shown in FIG. 1, the temporary pacing leads of FIGS. 2(b) and 2(c) cannot be positively attached to the heart wall of the atrium, and may be positively attached to the heart wall of the ventricle only when successfully being pushed into and lodged in the trabeculae carnae, or when mechanically biased against the endocardium.

Occasionally, pacing using prior art temporary leads may be accomplished using an electrode that floats in the blood filling the right atrium. Often, however, such floating electrodes are incapable of pacing the heart owing to insufficient electrical coupling between lead electrodes and the endocardium. The leads shown in FIGS. 1 through 2(c) rely on pacing through floating, lodged or mechanically biased electrodes. Pacing of the atrium using such leads is particularly difficult because no trabeculae are present in which a lead may be lodged, and mechanical biasing of such leads in the atrium requires curved portions having short radii, which often prove difficult to implant, and that further provide poor electrode to endocardium mechanical and electrical coupling.

Table 2 below shows comparative technical data respecting prior art temporary pacing leads and one embodiment of the present invention.

| VENDOR & MODEL NUMBER | LEAD TYPE | LEAD DIAM. (French) | LEAD LENGTH (cm's) | DISTAL SPACE (cm's) | DISTAL CURVE (degrees) | ELECTRODE MATERIAL | TIP SURFACE AREA (mm) | RING SURFACE AREA (mm) | CONECTOR TYPE (prox. end) | RATIO OF RING TO TIP SURFACE AREA |
|---|---|---|---|---|---|---|---|---|---|---|
| USCI 008556 | BIPOLAR BALLOON (1) | 5 FRENCH | 110-GREEN, MARKINGS | 1.0 | NONE | Stainless Steel | 1.66 × .087 11 mm area sqrd | 1.7 × 2 dim. 11 mm area sqrd | Bifurcated 11 mm area pins | 1 TO 1 unprotected |
| USCI 007153 | BIPOLAR | 6 FRENCH | 125-GREY, NO MRKGS | 1.0 | 60 | Platinum | 1.9 × 2.2 12..4 mm area sqrd | 2 × 2.2 dim. 14 mm area sqrd | Bifurcated with unprotected pins | 1.13 TO 1 |
| ELECATH 11-KBE2 | BIPOLAR BALLOON | 6 FRENCH | 110-BLUE MARKINGS | 1.2 | NONE | ?? | 1.3 × 5 19 mm area sqrd | 1.6 × 5 dim. 25 mm area sqrd | Bifurcated with unprotected pins | 1.3 TO 1 |
| ELECATH 22-0565 | BIPOLAR | 6 FRENCH | 110-WHITE NO MRKGS | 1.0 | 60 | ?? | 2 × 5 28 mm area sqrd | 2 × 4.7 dim. 29 mm area sqrd | Bifurcated with unprotected pins | 1 TO 1 |
| BAXTER 97-130 | BIPOLAR BALLOON | 5 FRENCH | 90 MARKINGS | 1.0 | J | ?? | 1.9 × 1.9 11 mm area sqrd | 2 × 3 dim. 19 mm area sqrd | Bifurcated with protected pins | 1.73 TO 1 |
| B. BRAUN TP-90-1 | BIPOLAR BALLOON | 5 FRENCH | 90-PINK MARKINGS | 1.2 | J | Platinum | 1.7 × 3.2 16 m area sqrd | 1.65 × 3.2 dim. 16.5 mm area sqrd | Bifurcated with protected pins | 1 TO 1 |

-continued

| VENDOR & MODEL NUMBER | LEAD TYPE | LEAD DIAM. (French) | LEAD LENGTH (cm's) | DISTAL SPACE (cm's) | DISTAL CURVE (degrees) | ELEC-TRODE MATER-IAL | TIP SURFACE AREA (mm) | RING SUR-FACE AREA (mm) | CONECT-OR TYPE (prox. end) | RATIO OF RING TO TIP SUR-FACE AREA |
|---|---|---|---|---|---|---|---|---|---|---|
| DAIG 401674 | BI-POLAR | 5 FRENCH | 110-GREEN MARKINGS | 1.0 | 60 | ?? | 1.7 × 3 14 mm area sqrd | 1.7 × 3.2 dim. 17 mm area sqrd | Bifurcated with unprotected pins | 1.2 TO 1 |
| MEDTRONIC CARDIO | BI-POLAR | 6 FRENCH | 110-BLUE NO MRKGS | 1.0 | J | Platinum | 1.9 × 1.4 8 mm area sqrd | 2 × 1.4 dim. 8.5 mm area sqrd | Bifurcated with unprotected pins | 1 TO 1 |
| MEDTRONIC 6704 | BI-POLAR | MORE THAN 4 FRENCH | 110-WHITE NO MRKGS | 1.0 & 2.5 | 52 & NONE | Stainless Steel | 1.3 × 3 12 mm area sqrd | 1.3 × 5 21 mm area | In-line pins | 1.75 TO 1 |
| ONE EMBODIMENT OF PRESENT INVENTION | BI-POLAR | 3.5 FRENCH | 78, 80, 90, 150 MARKINGS | 1.0 | NONE | 316 Stainless Steel | 4.26 mm squared | 17 mm squared | Bifurcated with unprotected pins that pass through catheter | 4 TO 1 |

Table 2 shows that the lead of the present invention not only has a higher ratio of ring electrode surface area to tip electrode surface area, but also a decreased tip electrode surface area in respect of prior art temporary pacing leads.

The ratio of ring electrode surface area to tip electrode surface area characteristic of the present invention is greater than or equal to 2:1, and may be greater than or equal to about 2.5:1, about 3:1, about 3.5:1, about 4:1, about 4.5:1, about 5:1 or 5:1. The higher this ratio becomes, the greater the ability of the lead to sense intra-cardiac events.

Additionally, the inventors discovered that the small surface area of the tip electrode in combination with the high ratio of the ring electrode surface area to the tip electrode surface area permits the voltage drop occurring across the tip electrode to be greater than the voltage drop occurring across the ring electrode. This is because the impedances of the respective electrodes are inversely related to their surface areas. Thus, the impedance of the tip electrode of the present invention is greater than the impedance of the ring electrode. This, in turn, results in a higher voltage, and a correspondingly higher voltage gradient, being delivered to the tissue surrounding the tip electrode than would otherwise be possible using conventional prior art electrodes. Higher voltages and voltage gradients result in better capture, lower thresholds for capture, and lower energy requirements for pacing. In the present invention, it is preferred that the relative impedances of the tip and ring electrodes be selected so that about two-thirds of the output voltage provided by the pacemaker appears across the tip electrode.

As shown in Table 2, the tip electrode of the present invention has a small surface area that is less than or equal to 10 square millimeters, and may be less than or equal to about 9.5 mm$^2$, about 9 mm$^2$, about 8.5 mm$^2$, about 8 mm$^2$, about 7.5 mm$^2$, about 7 mm$^2$, about 6.5 mm$^2$, about 6 mm$^2$, about 5.5 mm$^2$, about 5 mm$^2$, about 4.5 mm$^2$, about 4 mm$^2$, about 3.5 mm$^2$, about 3 mm$^2$, about 2.5 mm$^2$, about 2 mm$^2$, about 1.5 mm$^2$, about 1 mm$^2$. Most preferably, however, the surface area of the tip electrode is about 4 mm$^2$. The small surface area of the tip electrode of the present invention permits the delivery of high current densities to the capture site, and thus the use of lower capture thresholds. Although the total current delivered through the tip electrode of the present invention may be substantially the same as that delivered by prior art temporary leads, the current density provided by the tip electrode of the present invention at the capture site is greater than the current density that may be achieved using prior art temporary leads owing to the small surface area of the present invention's tip electrode.

In one bipolar embodiment of the present invention, the temporary pacing lead generally comprises the following elements: (a) a first electrode tip for delivering pulses of electrical energy to the endocardium, (b) a first electrical conductor attached at its distal end to the electrode tip and at its proximal end to a first electrical connector, (c) a second ring electrode spaced apart from the first electrode, (d) a second electrical conductor attached at its distal end to the ring electrode and at its proximal end to a second electrical connector, (e) biocompatible and electrically insulative material disposed between the first and second electrical conductors, (f) biocompatible and electrically insulative material for externally protecting and electrically insulating the conductors from body fluids. The lead is guided to an endocardial affixation site by means of an external guide catheter.

In one unipolar embodiment of the present invention, the temporary pacing lead generally comprises most or all the foregoing elements with the exception of the ring electrode, which it does not include. Instead a unipolar temporary pacing lead of the present invention may utilize a pacemaker can or a patient's skin as the second electrode. It is worth noting, however, that in practice the temporary leads of the present invention will rarely be connected to implantable pacemakers because external pulse generators are almost always used in temporary pacing applications.

FIGS. 3 through 12 show a proposed commercial embodiment of, and test data related to, the present invention, the MEDTRONIC™ Model No. 6416 Active Fixation Lead. The present invention is not limited in scope to the particular embodiment of the present invention shown in FIGS. 3 through 12.

Figure 3:
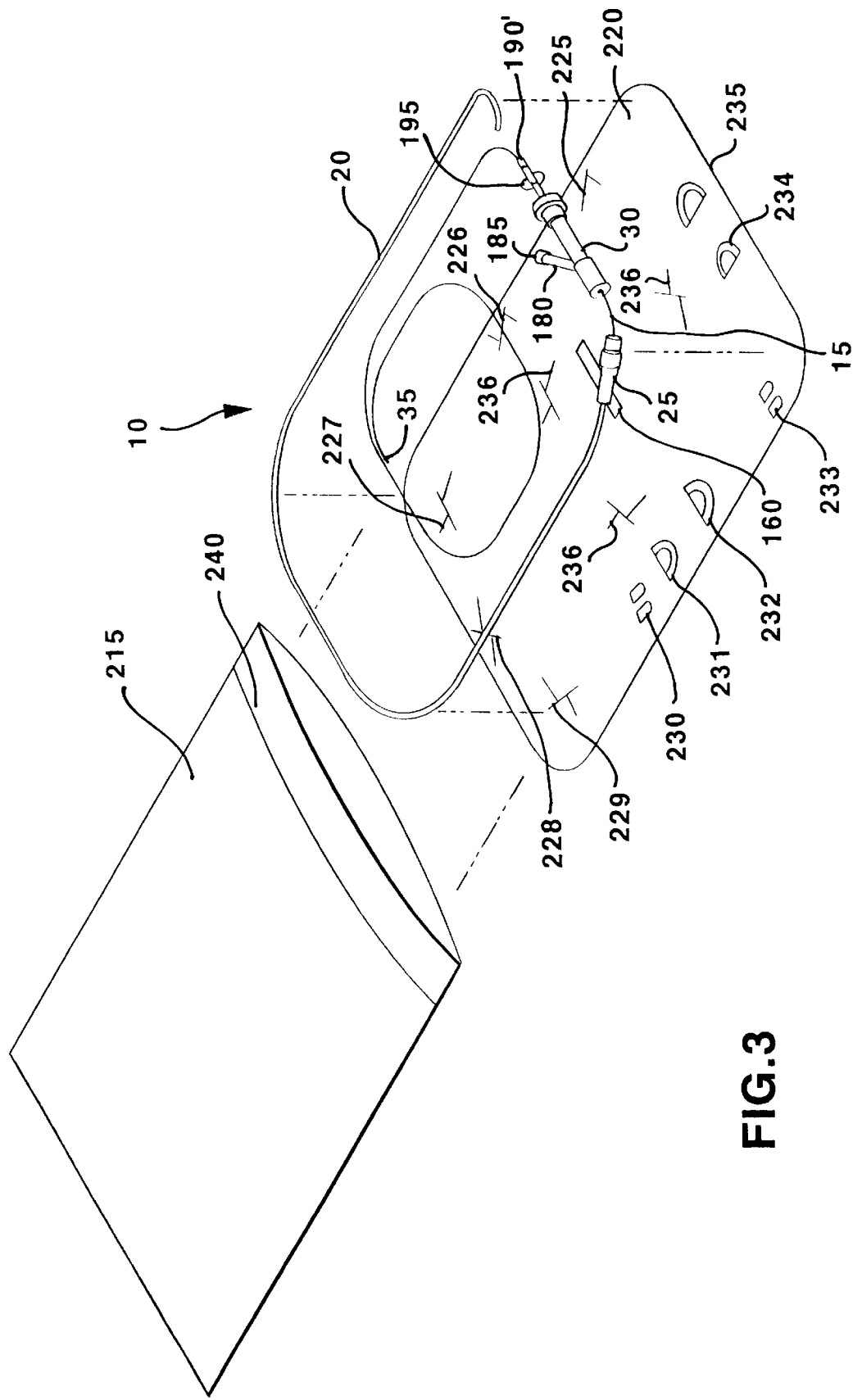
FIG. 3 shows a right perspective view of one embodiment of the temporary pacing lead assembly of the present invention and corresponding optional insert card and pouch.

FIG. 3 is a right perspective view of one embodiment of the present invention, where lead assembly 10 comprises guide catheter 20 and lead body 15. For packaging and shipment purposes optional insert card 220 receives and holds lead assembly 10 in insert card flaps 225–236. Insert card 220 and lead assembly 10 fit within pouch 215, which is preferably sealed thermally by seal 240. The complete assembly 10, insert card 220 and pouch 215 should be 100% ethylene oxide sterilized. Portions of pouch 215 are most preferably fabricated of transparent plastic or the like to permit observation of lead assembly 10 and any identifying indicia that may be printed thereon without seal 240 having to be broken.

Lead body 15 is received by and fits slidingly within guide catheter 20. Hub 25 is located at the proximal end of guide catheter 20, and has label 160 disposed on the outer surface thereof. Label 160 may have a control number or other identifying indicia printed thereon for purposes of rapidly and accurately identifying lead assembly 10. Hemostasis valve 30 may be attached to the proximal end of hub 25. Removal of screwably attaching sealing cap 185 from neck 180 permits the introduction of saline solution, anticoagulants, intravenously administered drugs, and the through valve 30. The proximal end of valve 30 receives lead body 15 and guides it through hub 25 into guide catheter 20. Optional torque transfer tool 190 has a central longitudinal bore for accepting lead body 15 therewithin. Tool 190 may have wings 195 for transferring torque applied by a user to the proximal end of lead body 15 to the distal end thereof. Wings 195 have been discovered to work about as well as fingers applied directly to the lead body, and so are optional.

Figure 4:
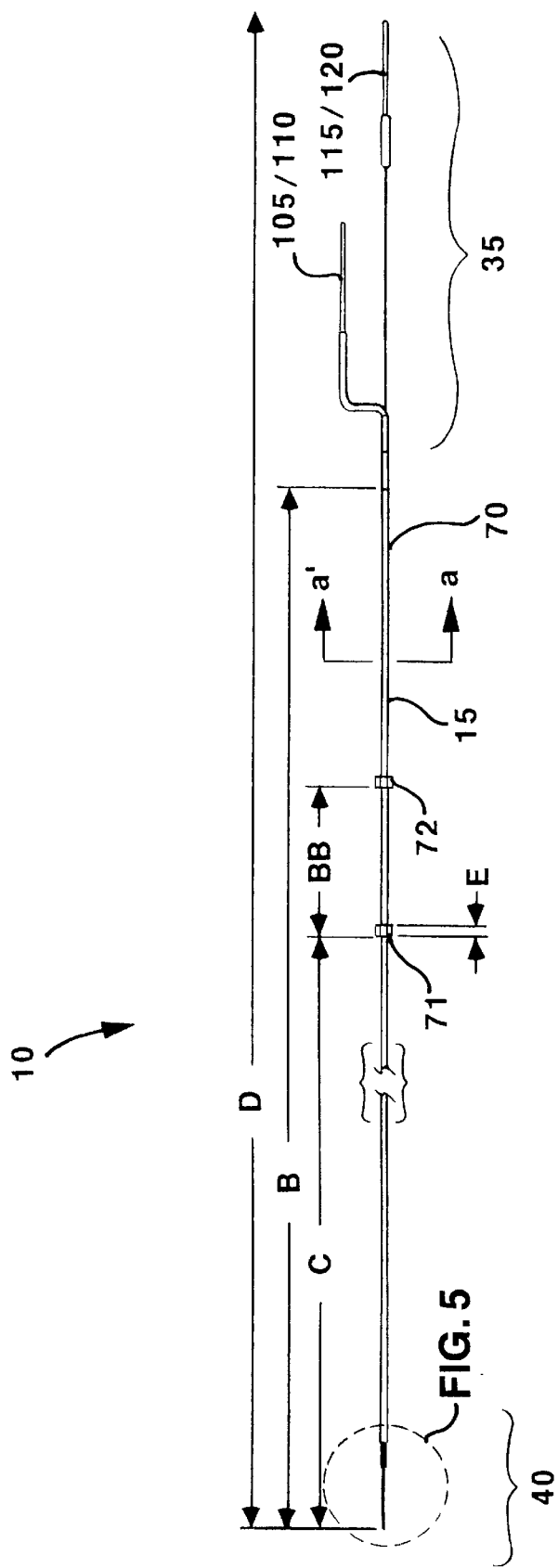
FIG. 4 shows a side view of one embodiment of the lead body of the present invention.

FIG. 4 is a side view of the lead body of one embodiment of the present invention. Lead body proximal end 35 has two connectors, first connector 105 and second connector 115, for establishing electrical connection between lead assembly 10 and an external or temporary pacemaker. Connectors 105 and 115 may be positive and negative terminals, respectively, or vice-versa, depending on the particular application at hand, the implanting physician's desires, and the type of external pulse generator or pacemaker used. As shown in FIGS. 3 and 4, connectors 105 and 115 are most preferably pin connectors 110 and 120. Other types of connectors, however, fall within the scope of the present invention.

As shown in FIG. 4, first connector 105 and second connector 115 have a low profile staggered pin design. The staggered design advantageously permits guide catheter 20 to be withdrawn over the first and second connectors.

Depth markers 71 and 72 are used by the physician to gauge the extent to which lead body 15 has been inserted in the patient. Depth marker 72 is used to gauge the extent of insertion of lead body 15 only when hemostasis valve 30 is attached to the proximal end of lead body 15. Otherwise, depth marker 71 is used to gauge the extent of insertion of lead body 15. Depth markers 71 and 72 may be formed of polyethylene heat shrink, or printed on lead body 15 using medical grade ink.

An active fixation mechanism is attached to the distal end of lead body 15. Examples of active fixation mechanisms falling within the scope of the present invention include, but are not limited to, helical screws, automatic sutures, fishhook devices, needles, barbs, and the like. In the present invention, active fixation mechanisms that may be easily removed from the myocardium and endocardium are preferred.

Electrically insulative outer sheath 70 is formed of biocompatible material such as a suitable polyurethane or silastic compound, and protects electrical conductors disposed within lead body 15 from the corrosive effects presented by body fluids. Sheath 70 additionally prevents the outermost conductor disposed within lead body 15 from shorting out electrically to the body. A preferred material for outer sheath 70 is NESTE NCPE 8020 polyethylene.

First electrical connector 105 and second electrical connector 115 are located at lead body proximal end 35, and comprise first pin connector 110 and second pin connector 120, respectively. First and second pin connectors 110 and 120 are most preferably formed of 316 stainless steel, and are adapted to be connected to the positive and negative leads of an external pace generator, or EPG. The distal portions of the two pin connectors are preferably sheathed by polyethylene or polyolefin heat shrink as a means of electrically insulating the connectors from one another and body fluids.

Guide catheter 20 and lead body 15 may be configured to have lengths appropriate for pediatric use, use in persons having different body sizes, or implantation through different entry points such as the left or right subclavian vein, the internal jugular vein, or the right or left femoral veins. Additionally, guide catheter 20 and lead body 15 may be configured to have lengths appropriate for implantation in the right atrium or the right ventricle. Relatively direct stimulation of the left atrium or left ventricle using the present invention may become possible at some future date by, for example, positioning the tip electrode sufficiently close to the interior wall of the left atrium or left ventricle through entry from the right atrium or right ventricle, respectively.

Figure 5:
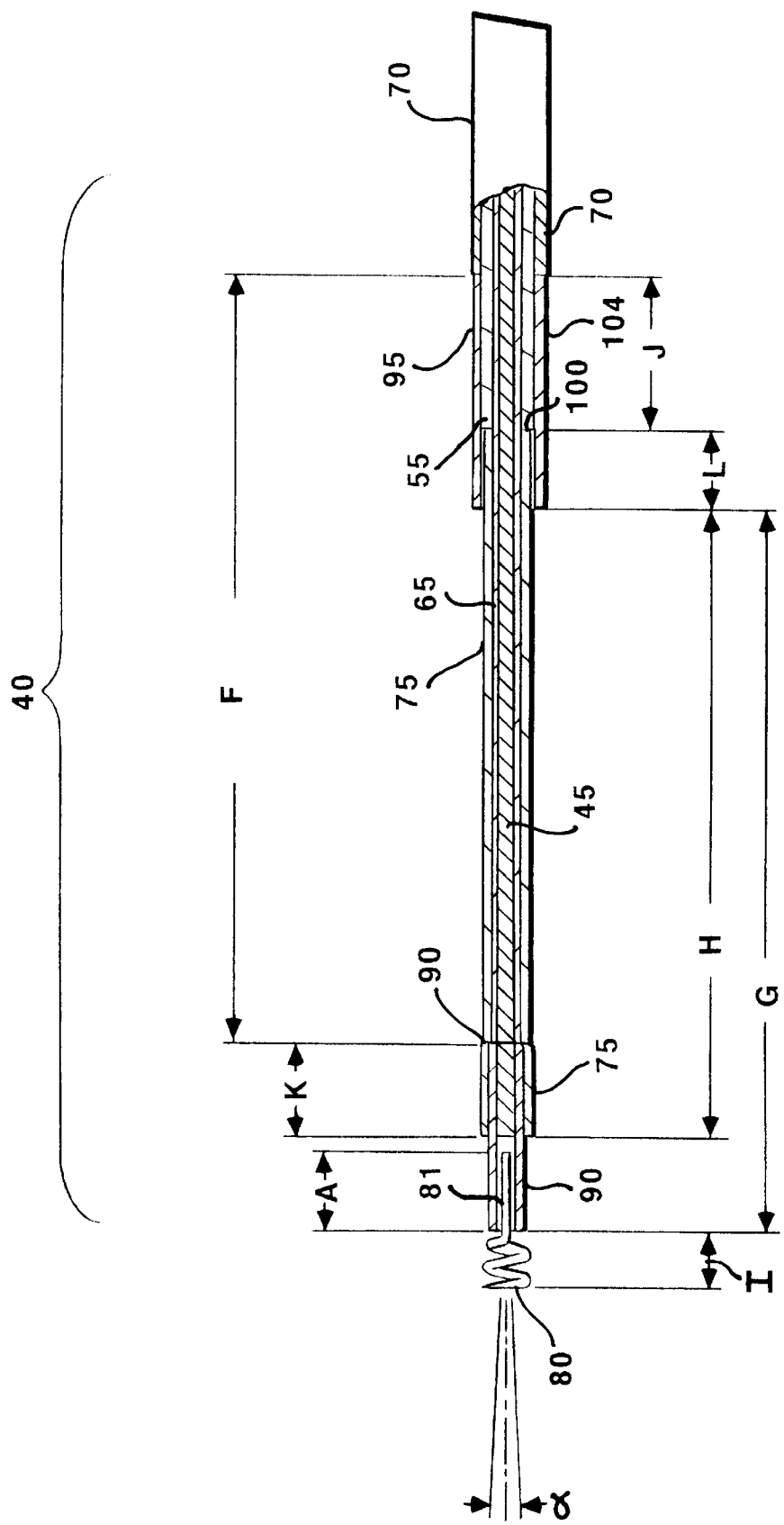
FIG. 5 shows an enlarged axial cross-sectional view of one embodiment of the central portion of the lead body shown in FIG. 2.

FIG. 5 is an enlarged axial cross-sectional view of lead body distal end 40. Most preferably, inner conductor 45 comprises three strands of left-hand-wound twisted stainless steel wire, and is capable of reliably conducting electrical current after having been subjected to numerous, repeated bending and torquing stresses. Less preferably, inner conductor 45 may comprise a single wire formed of a nickel-titanium alloy such as NITINOL™. Lead body 15 most preferably has a diameter of about 3.5 French, but may have a diameter as great as about 3.98 French or as small as about 2 French.

Multiple twisted or braided inner conductor wires have been discovered to provide the optimum combination of a lead body that maintains small diameter yet still transfers torque efficiently between its proximal and distal ends. In the present invention, more or fewer than three wires may be employed to form inner conductor 45. Three wires, however, have been discovered to provide the best overall combination of maximum strength, minimum diameter, and maximum torque transfer between proximal and distal ends.

In one embodiment of the present invention, the wires of inner conductor 45 shown in FIG. 5 are supplied by Axon Wire of Montmirail, France and formed of medical grade 316L stainless steel wire or cable material. Each wire preferably has a diameter of between about 0.002 and about 0.006 inches, and most preferably has a diameter of about 0.004 inches. Inner conductor 45 may optionally comprise wires formed of a nickel-titanium alloy such as NITINOL™, platinum, gold, silver, palladium, other noble metals, and other alloys or metals suitable for use in the human body. NITINOL™ may be purchased from Fort Wayne Metals of Fort Wayne, Ind.

In a preferred embodiment of the present invention, outer conductor 55 shown in FIG. 5 most preferably comprises sixteen metallic braided wires formed of 316L medical grade stainless steel wire or cable, and is capable of reliably conducting electrical current after being subjected to numerous repeated bending and torquing stresses. In the present invention, more or fewer than sixteen wires may be employed to form outer conductor 55. For example, anywhere from 4 to 32 wires may be employed to form outer conductor 55. Sixteen wires, however, have been discovered to provide the best overall combination of maximum strength, minimum diameter, and maximum torque transfer between proximal and distal ends. The inventors discovered that the braided or twisted wires forming the outer conductor transfer most of the torque applied to the proximal end of the lead to its distal end.

In a preferred embodiment of the present invention, the wires of outer conductor 55 shown in FIG. 5 are supplied by AXON WIRE™ of Montmirail, France and are formed of medical grade 316L stainless steel wire or cable material. Each wire preferably has a diameter of between about 0.0015 and 0.004 inches, and most preferably has a diameter of about 0.0025 inches. Outer conductor 55 may optionally comprise wires formed of platinum, gold, silver, palladium, other noble metals, and other alloys or metals suitable for use in the human body.

In the embodiment of the invention shown in the FIGS. 3 through 9, inner conductor 45 is mechanically and electrically connected to second connector 115, and outer conductor 55 is mechanically and electrically attached to first connector 105. It is preferred that the DC resistance of lead body 15 not exceed about 50 Ohms per meter for the combined total resistance of the strands or wires forming the inner conductor, and not exceed about 30 Ohms per meter for the combined total resistance of the strands or wires forming the outer conductor.

As shown in FIG. 5, electrically insulative layer 65 separates and electrically insulates inner and outer conductors 45 and 55 from one another. Layer 65 is preferably formed of a fluoro-copolymer such as fluorinated ethylene propylene (FEP) or TEFLON 100™, but may also be formed of nylon or any other suitable material. FEP is a preferred insulation material because of the low shrink ratio it exhibits upon being subjected to heat. Suitable FEP insulation may be obtained from TFX MEDICAL CORPORATION™ of Massachusetts. Distal heat shrink tubing 75 is also preferably formed of FEP, and is disposed over the outer surface of first distal mechanical crimp joint 90, which in turn retains helical retainer shank 81 of helical screw-in retainer 80. Dimension L in FIG. 5 is a region where it is preferred to overlap layers of FEP insulation in the area just distal from braided wire junction 100. The two overlapped layers of FEP insulation in this region provide stress relief from flex fatigue. Dimension J of second mechanical crimp 104 is the region over which mechanical crimping forces are applied to mechanically and electrically connect ring electrode 95 to underlying outer conductor 55.

The configuration and structure of the inner and outer conductors, and the wires that form them, permits the lead of the present invention to resist flex fatigue better than most known leads. This is because the lead of the present invention is highly flexible and nearly limp when implanted, resulting in reduced moment or torque acting on the lead body and reduced pressure acting on the distal tip of the lead as the lead flexes in response to the heart beating or other tissue moving.

Helical screw-in retainer 80 of FIG. 5 is preferably formed of 316 stainless steel, and may be obtained from JER-NEEN SPRING, INC.™ of Forest Lake, Minn. Screw-in retainer 80 is most preferably formed such that it penetrates tissue at a rate of about 0.016 inches per turn, or has a pitch of 0.016 inches. The retainer of the present invention may have a pitch other than 0.016 inches per turn, and may range anywhere between about 0.008 and about 0.040 inches per turn, between about 0.014 and about 0.018 inches per turn, between about 0.012 and about 0.020 inches per turn, between about 0.010 and about 0.025 inches per turn, or between about 0.010 and about 0.030 inches per turn.

Helical screw-in retainer 80 engages endocardial tissue and may penetrate into myocardial tissue upon rotational torque being applied by the implanting physician to the proximal end of lead body 15 when retainer 80 is appropriately positioned inside the heart. Helical retainer shank 81 fits inside a first sleeve 90, and is crimped mechanically thereto. Although the specific crimping means used to mechanically couple shank 81 and first distal mechanical crimp joint 90 together are a matter of choice, in the most preferred embodiment of the present invention the crimping should be done atraumatically. First mechanical crimp joint 90 also serves as tip electrode 90. Dimension A of first mechanical crimp 90 is the region over which mechanical crimping forces are applied to mechanically and electrically connect tip electrode 90 to underlying inner conductor 45.

It is well known that large diameter leads and leads having active fixation mechanisms may cause excessive trauma to venous and cardiac tissues during implantation procedures. Often it is difficult or even impossible to accurately control the depth of penetration of some active fixation mechanisms into the myocardium during implantation. This problem is especially apparent in helically wound electrode tips. As a result, the risk of perforating the atrium or ventricle during implantation may be heightened when active fixation mechanisms similar to those of the present invention are employed. Further exacerbating this problem is the fact that venous, heart valve and other cardiac tissue often cannot be protected from active fixation devices during implantation owing to their relatively large size, unless expensive protective sheathing structures are employed at the distal end of the lead to protect such tissue from the device until it is delivered to the affixation site; only then may such structures be retracted or otherwise removed from around the device. Finally, active fixation mechanisms can cause substantial trauma and scarring of cardiac tissue when a lead having such a device is removed.

On the other hand, active fixation devices typically provide optimum electrical coupling of the tip electrode to cardiac tissue. This is an important advantage in the context of temporary leads because heretofore such leads have been unable to provide consistently good electrode-tissue electrical coupling, and as a result their use rarely included non-pacing diagnostic applications such as cardiac output tests, cardiac stress tests and the like, where high signal-to-noise ratios and good coupling were required.

The active fixation devices of the present invention are designed to have a limited depth of penetration into myocardial tissue, and thus to reduce the risk of perforation. In the present invention, the helical coil preferably penetrates cardiac tissue to a preferred maximum approximate depth of about 0.032 inches, which corresponds to only two complete revolutions of the lead body. This preferred maximum depth of penetration has been discovered to provide consistently excellent mechanical and electrical coupling to cardiac tissue under most conditions.

In contrast, prior art active fixation leads have helical coils having both larger diameters and higher pitches than that of the present invention. Thus, prior art leads having helical coil active fixation devices typically penetrate cardiac tissue to a depth approximating twice that of the present invention for an equal number of turns or revolutions of the lead body or other torque transfer mechanism. Excessive depth of penetration and consequent perforation of the heart wall is a common cause of lead dislodgment. It is an advantage of the present invention, therefore, that the occurrence of such perforation and consequent dislodgment is reduced respecting prior art leads.

The active fixation devices of the present invention preferably penetrate cardiac tissue to maximum approximate depths of about 0.010, about 0.014, about 0.018, about 0.022. about 0.026, about 0.030, about 0.036, or about 0.040 inches. Active fixation devices of the present invention and adapted for penetrating the ventricular myocardium may penetrate even deeper than 0.040 inches.

As described further below, this limited depth of penetration is permitted by the low pitch and small number of turns characterizing the helical coil. The risk of perforation is reduced further in the present invention by the helical coil having a smaller diameter than has heretofore been employed in pacing applications, the lead body having increased flexibility and malleability respecting prior art temporary leads, and the wire forming the helical coil having a small diameter.

The active fixation feature of the present invention further increases electrode-tissue electrical coupling and therefore increases the likelihood and strength of capture in pacing applications, thereby reducing patient risk. The active fixation feature of the present invention also permits diagnostic, non-pacing procedures to be effected that heretofore were impossible or very difficult to accomplish with prior art temporary pacing leads.

The active fixation feature of the present invention permits a physician to position and place the tip electrode with a degree of accuracy that heretofore has been unattainable using prior art temporary pacing leads. Moreover, the active fixation feature of the present invention permits the tip electrode to be attached to heart wall locations to which prior art temporary pacing leads simply cannot be affixed. For example, the tip electrode of the present invention may be employed to pace the heart at a location high in the septum near the Bundle of His. Tip electrodes of prior art temporary pacing leads cannot be attached to the heart wall at such a location. Pacing in this location may result in improved cardiac output because the ventricular myocardia depolarize more synchronously.

To prevent perforation of the heart wall, it is preferred that helical coil retainer 80 not "worm hole" deeper into the myocardium when lead body 15 is rotated more than two revolutions. Testing of retainer 80 has shown that retainer 80 of the present invention does not burrow more deeply into the myocardium when the lead body is over-rotated because the central, core portion of the retainer fills with myocardial tissue and resists rotation. As over-rotation of the retainer continues, lead body 15 buckles under the torque load, and further rotation is prevented.

As shown in Table 2, the tip electrode of the present invention has a small surface area that is less than or equal to 10 square millimeters, and may be about 9.5 mm$^2$, about 9 mm$^2$, about 8.5 mm$^2$, about 8 mm$^2$, about 7.5 mm$^2$, about 7 mm$^2$, about 6.5 mm$^2$, about 6 mm$^2$, about 5.5 mm$^2$, about 5 mm$^2$, about 4.5 mm$^2$, about 4 mm$^2$, about 3.5 mm$^2$, about 3 mm$^2$, about 2.5 mm$^2$, about 2 mm$^2$, about 1.5 mm$^2$, about 1 mm$^2$, or less 1 mm$^2$.

The degree of positive fixation provided by the helical coil retainer of the present invention was quantified as follows. Four retainers 80 were rotated two complete revolutions into canine heart tissue. Each retainer was then subjected to a measured tensile force which gradually increased until retainer 80 pulled out of and separated from the bulk of the heart tissue. No rotation of retainer 80 was permitted while tensile forces were being applied. It was discovered that an average of 0.45 pounds of tensile force were required for retainer 80 pull out of and separate from the bulk of the heart tissue.

This result is significant in view of the fact that no prior art temporary lead known of by the inventors can be positively affixed to the heart wall, and thus no known prior art temporary leads can provide any meaningful resistance to a pulling or tensile force. The distal ends of known prior art temporary leads have no tines, flanges, or any other securing means attached thereto which permit positive affixation to the heart wall.

The lead of the present invention most preferably provides positive affixation to the heart wall such that at least 0.40 pounds of tensile force are required for the active fixation device to pull out of and separate from the bulk of the heart tissue. Tensile forces less than 0.40 pounds are contemplated in the present invention, however. For example, the present invention may provide less than about 0.10 pounds of tensile force, less than about 0.15 pounds of tensile force, less than about 0.20 pounds of tensile force, less than about 0.25 pounds of tensile force, less than about 0.30 pounds of tensile force, or less than about 0.35 pounds of tensile force before the active fixation device pulls out of and separates from the bulk of the heart tissue.

Figure 6:
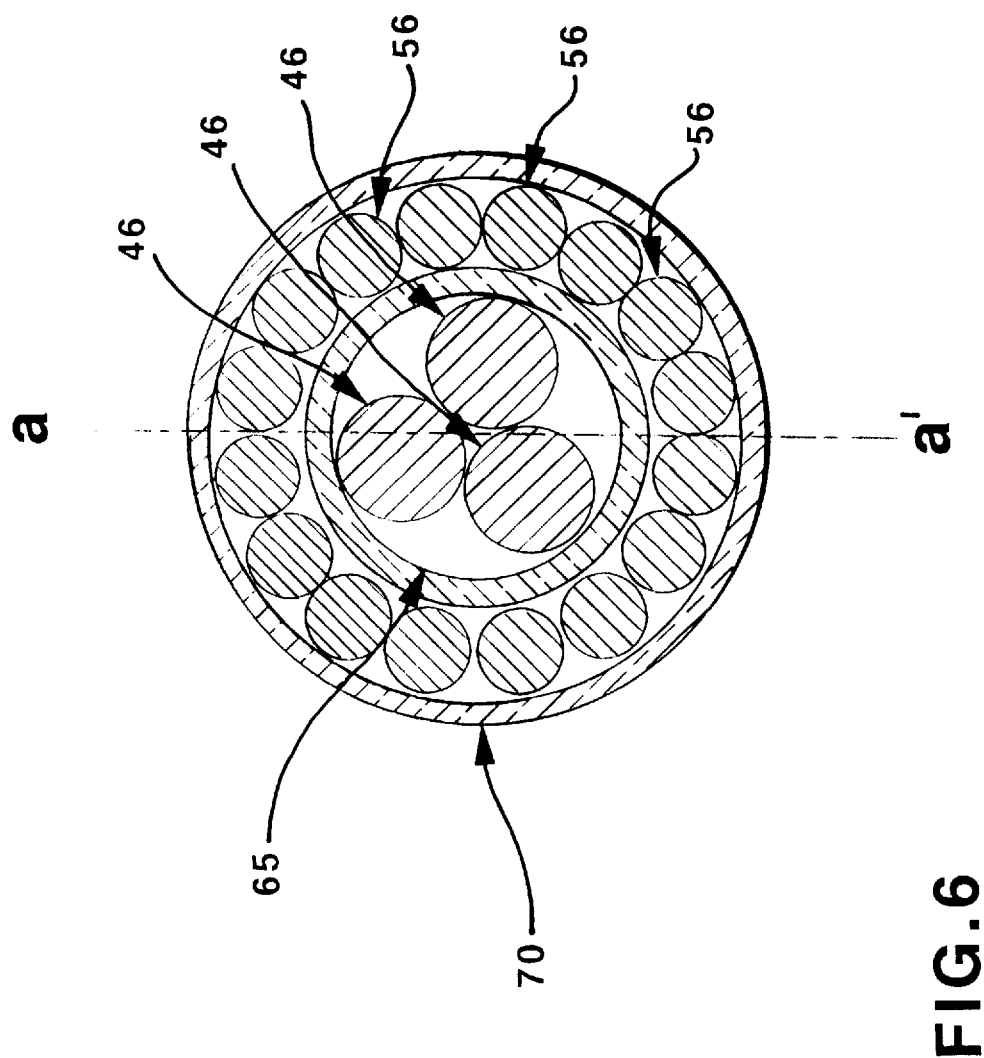
FIG. 6 shows an enlarged radial cross-sectional view of one embodiment of the lead body of the present invention taken along line a–a' in FIG. 4.

FIG. 6 is an enlarged radial cross-sectional view of a central portion of lead body 15 taken along line a–a' in FIG. 4. Inner conductor 45 preferably comprises a plurality of wires 46, and most preferably comprises 3 strands of twisted wire. Inner electrically insulative layer 65 separates inner conductor 45 from outer conductor 55. Outer conductor 55 comprises a plurality of wires 56, and most preferably comprises 16 wires braided together. Electrically insulative and biocompatible outer sheath 70 protects wires 56 from body fluids.

Figure 7:
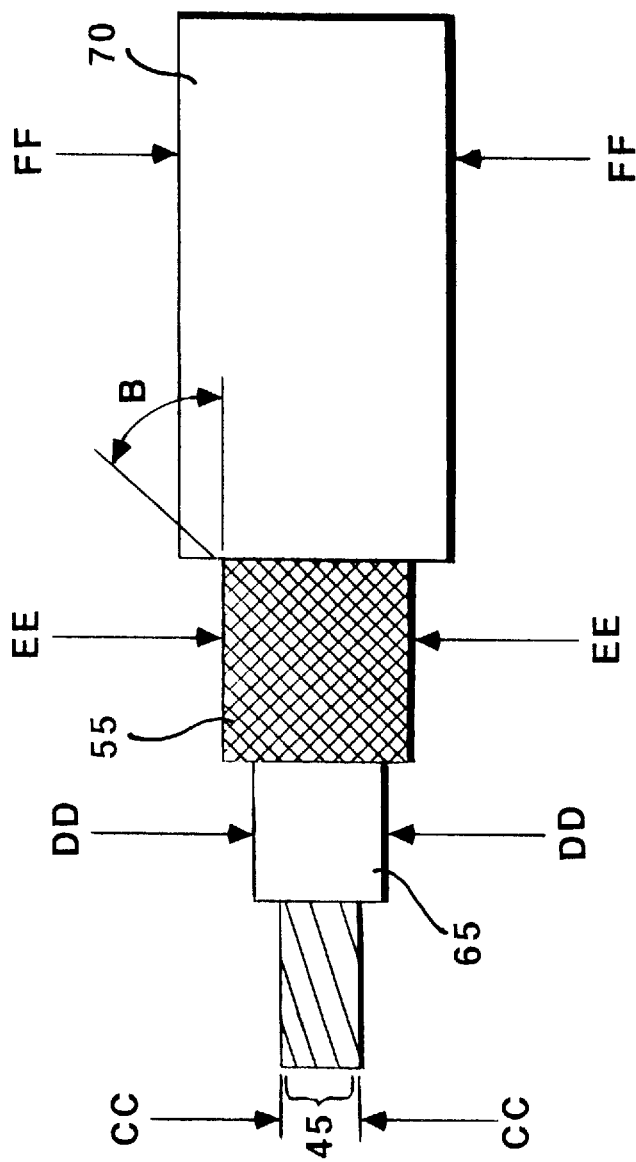
FIG. 7 shows a side cutaway view of one embodiment of the lead body of the present invention.

FIG. 7 shows a side cutaway view of one embodiment of the lead body of the present invention. Most preferably, inner conductor 45 comprises three left-hand-wound twisted wires formed of AISI 316L stainless steel that meets AISI A580—Stainless and Heat-Resisting Steel Wire, Military W81822A and DIN 46 399 specifications. Inner conductor 45 is preferably of true concentric construction, and contains 3 left-hand-wound wires having 14, plus or minus 3, twists per inch. The diameter of each wire is most preferably about 0.004 inches. The diameter of the inner conductor is most preferably about 0.008 inches (see dimension CC in FIG. 7). Inner insulative layer 65 is preferably formed of FEP, and preferably has an outer diameter of about 0.019 inches, plus or minus 0.001 inches (see dimension DD in FIG. 7).

Outer conductor 55 preferably comprises 16 wires woven in a helicoidal, braided pattern to form a shield, where 8 wires have a first orientation, and the remaining 8 wires have a second orientation forming an oblique angle to the first orientation. Each wire preferably has a diameter of about 0.0025 inches. Wires forming outer conductor 55 should meet the same general test specifications as those forming inner conductor 45.

Each wire in the second conductor is preferably 0.0025 inches in diameter. When the inner and outer insulation are stripped for a length of 5 mm, the inner and outer conductors should not lose their stranded or braided configurations.

Dimension EE of FIG. 7 is about 0.027 inches. Shield angle β is nominally set at 60 degrees. The outer diameter of lead body 15 forming the outer surface of insulative outer sheath 70 is preferably 0.044 inches, plus or minus between about 0.001 and about 0.002 inches.

In a bipolar electrode configuration of the present invention, lead body 15 preferably withstands a minimum tensile load of 10 lb. without breaking. Inner and outer conductors 45 and 55 preferably should each withstand a minimum tensile load of 3 lb. without breaking, and without experiencing an elongation exceeding 35%. When tested in accordance with Military Standard W81822 A, the force required to pull off outer sheath 70 or inner insulative layer 65 should be no less than 0.562 lb. and no greater than 3.37 lb., except when the unstripped length is 41.3, plus or minus 1.6 mm, the pull speed is 100±10 mm/min.

Figure 8:
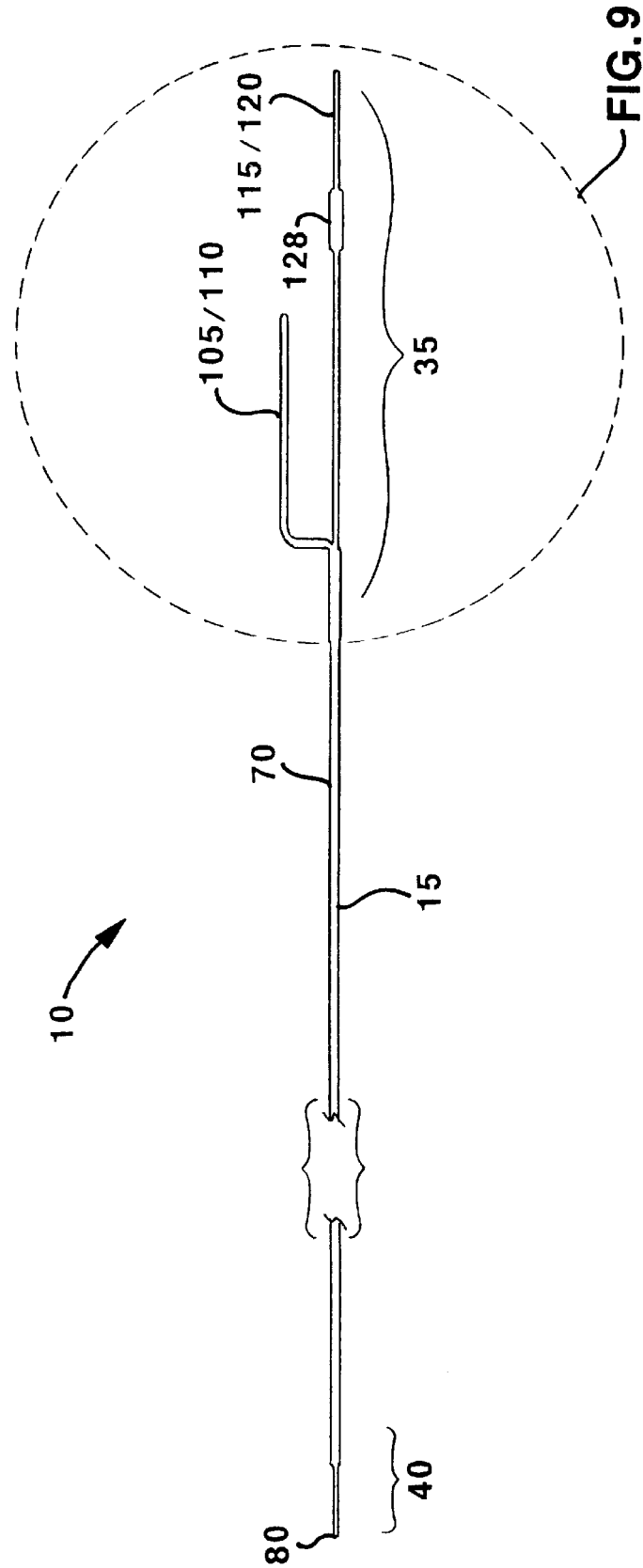
FIG. 8 shows a side view of an embodiment of the lead body of the present invention.

FIG. 8 is a side view of one embodiment of lead assembly 10 of the present invention, where lead body proximal end 35 is shown slightly enlarged respecting FIG. 4. Heat shrink sleeve 128 covers the mechanical and electrical connection established between pin 120 and the proximal end of inner conductor 45 by crimping sleeve 127, and provides strain relief from flex fatigue for the second pin connector.

Figure 9:
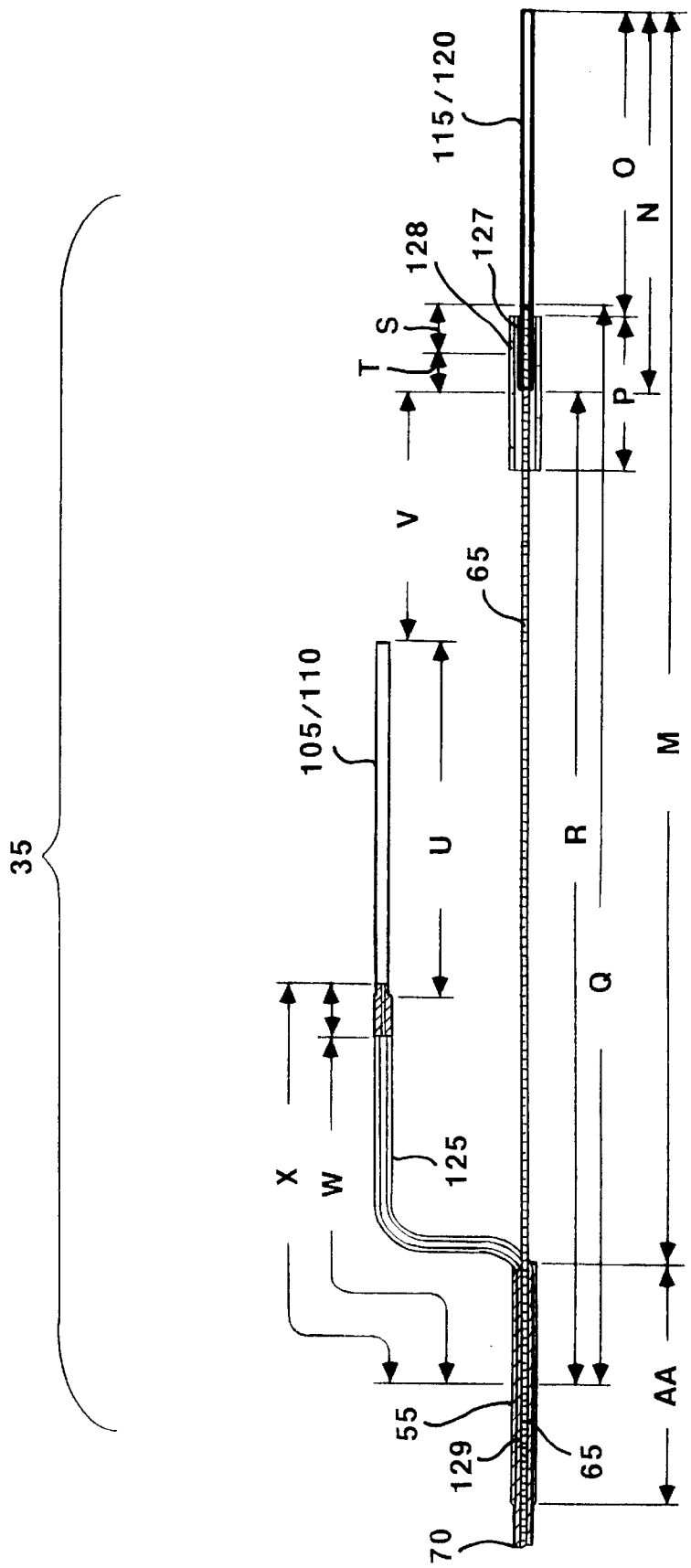
FIG. 9 shows an enlarged view of one embodiment of the proximal end of the lead body of the present invention.

FIG. 9 is an enlarged view of lead body proximal end 35 and the connectors shown in FIG. 8. FEP heat shrink 125 covers outer conductor 55 between lead body 15 and the distal portion of first pin connector 110, and mechanically connects the distal portion of pin 110 to outer conductor 55. Crimping sleeve 127 mechanically and electrically crimps second pin connector 120 onto inner conductor 45. FEP inner insulation layer 65 covers inner conductor 45 its entire length, except where mechanical and electrical connections are established to the tip electrode and the second pin connector. FEP heat shrink sleeve 129 mechanically binds inner conductor 45 and outer conductor 55 at the junction where they separate for connection to the distal ends of first and second pin connectors 110 and 120, respectively.

FIG. 10(a) is a left perspective view of one embodiment of guide catheter 20 and corresponding proximal hub 25 of the present invention. Guide catheter 20 is most preferably a MEDTRONIC™ Model No. MB-1 SHERPA™-series catheter. Preferred lengths of guide catheter 20 are 40, 60 and 90 cm corresponding to preferred lengths of lead body 15 of 100, 140 and 200 cm, respectively. Those lengths correspond, respectively, to the lead lengths required for implantation through the subclavian, inferior jugular and femoral entry sites. Guide catheter 20 has proximal end 130, distal end 135, and guide catheter body 147 disposed therebetween.

Guide catheter 20 is most preferably formed of PEBAX (polyether block amide) available from Adochem Corporation of Massachusetts. PEBAX is a preferred material for guide catheter 20 because of its kink resistance, durability, good shear resistance characteristics, and because it is available in a range of hardnesses.

As shown in FIG. 10(b), guide catheter 20 most preferably comprises outer jacket 22, inner liner 23, and sheath 29 formed most preferably of 16 braided stainless steel wires 24 disposed between the jacket and the liner. Sheath 29 provides torsional stiffness to lead assembly 10, prevents guide catheter 20 from kinking during implantation, and also helps maintain the shape imparted to guide catheter 20 by a physician prior to implantation. Each of stainless steel wires 24 has a preferred diameter of 0.0023 inches. Outer jacket 22 is preferably formed of 70D Shore A hardness scale PEBAX. Inner liner 23 is also preferably formed of 70D PEBAX. Soft tip 210 of guide catheter is preferably between about 0.125 inches and about 0.25 inches long, and formed of 40D PEBAX. The adjoining section joint region just proximal from tip 210 is about 1 inch long, and most preferably formed of injection molded 63D PEBAX.

The inner diameter of guide catheter 20 is preferably about 0.055 inches (4.2 French) or less. The outer diameter of guide catheter 20 is preferably about 0.078 inches (about 6 French) or less. In the embodiment of the invention shown in FIGS. 3–11, guide catheter 20 forms a tubular shape and receives therewithin a lead body having an outer diameter of about 4 French or less. The outer surface of what might otherwise be substantially non-torqueable lead body 15 engages the inner surface of guide catheter 20, which, in turn, laterally restrains lead body 15 and acts as a load or bearing surface upon which axial forces imparted to lead body 15 from the physician act, thereby permitting the transfer of torque through lead body 15 from its proximal to distal ends. It is this feature or aspect of the invention that permits a small-diameter, unobtrusive and limp lead body to be positively affixed to the heart wall at a selected site.

FIG. 10(a) shows guide catheter proximal end 130 having optional hub 25 attached thereto, where hub distal end 150 is attached to the proximal end of guide catheter body 21 by strain relief tubing 200. Strain relief tubing 200 is most preferably formed of PVC. Hub 25 is most preferably a Luer Hub formed of molded ABS, and comprises hub shoulders 157, hub distal end 150, and hub proximal end 155. Hub 25 has first bore 165 disposed generally along the longitudinal axis defining all but the distal end of guide catheter 20 and hub 25. First bore 165 has a tapered inner diameter, where the proximal end of first bore 165 has a diameter greater than that of the distal end of first bore 165.

Hub proximal end 155 preferably has one or more threads 165 disposed on the exterior surface thereof for receiving Y-adapter hemostasis valve 30. Lead body 15 is threaded through such a valve into hub 25 and guide catheter 20. Hemostasis valve 30 most preferably has an o-ring for engaging the outer circumference of lead body 15 to prevent the backflow of blood or other fluids through the valve during implantation.

Figure 11:
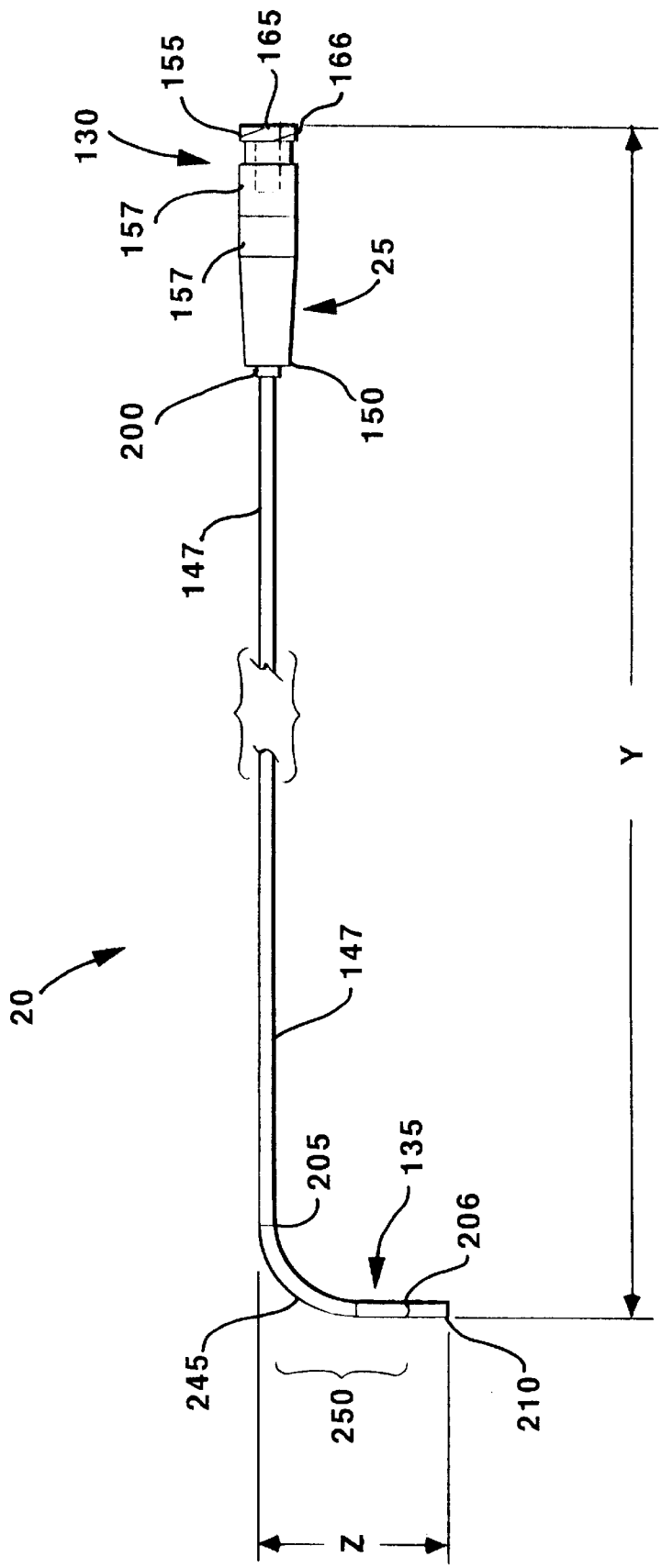
FIG. 11 shows a plan view of the guide catheter and hub shown in FIG. 10(*a*).

FIG. 11 is a side view of the guide catheter and hub shown in FIGS. 10(a) and 10(b). J-shaped guide catheter distal end 250 contains soft tip wire braid 245, which is formed by reducing the number of wire strands in sheath 29. Soft tip wire braid 245 extends between first segment joint 205 and second segment joint 206. Sheath 29 is not present in soft tip 210 to reduce the tip's stiffness and rigidity. Additionally, tip 210 is formed of PBEX having a lower durometer rating or hardness than corresponding to guide catheter body 147.

Figure 12:
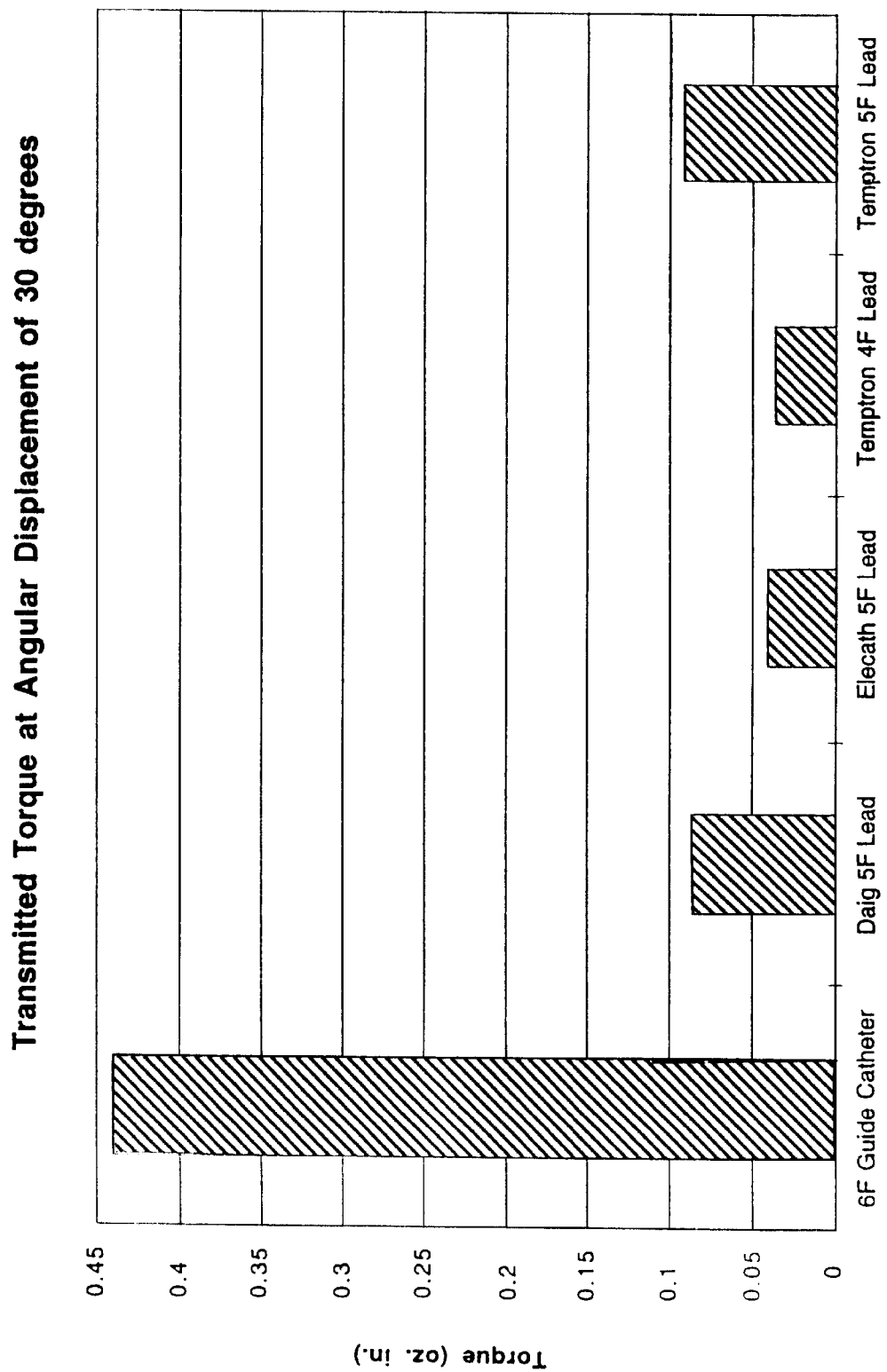
FIG. 12 compares the torque transmitted by the temporary lead of the present invention to the torques transmitted by various prior art temporary leads for a fixed angular displacement of thirty degrees.
Figure 13:
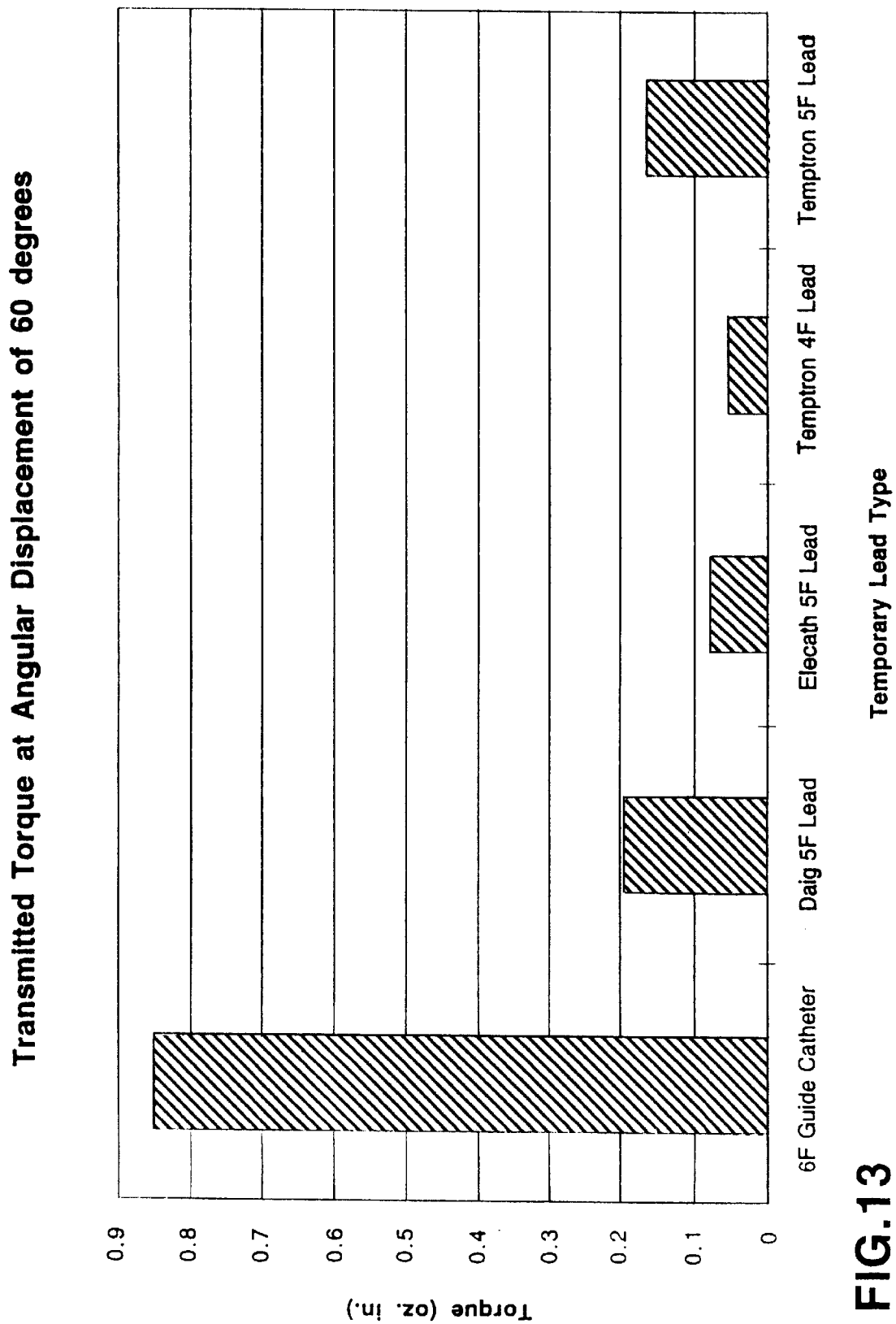
FIG. 13 compares the torque transmitted by the temporary lead of the present invention to the torques transmitted by various prior art temporary leads for a fixed angular displacement of sixty degrees.

Table 3 below sets forth torque versus angular displacement data obtained using different prior art temporary endocardial pacing leads and the lead of the present invention. FIGS. 12 and 13 are visual representations of the data presented in Table 3, where transmitted torque data for positive and negative angular displacements of the same magnitude are averaged for each temporary lead tested. FIG. 12 shows the average torque transmitted by selected prior art temporary leads and the lead of the present invention for angular displacements of plus and minus thirty degrees. FIG. 13 shows the average torque transmitted by selected prior art temporary leads and the lead of the present invention for angular displacements of plus and minus sixty degrees.

Data presented in Table 3 and shown in FIGS. 12 and 13 were obtained as follows. A first end of a ten-inch long sample of the guide catheter of the present invention or a prior art lead body was held in a fixed position by a clamping device, rendering the first end of the sample length immovable. The second opposing end of the sample was placed in the chuck of a torque watch device and firmly secured thereto. The length of each sample between the first and second ends was constrained so that the sample could not move horizontally and was co-axially aligned with the center of the torque watch chuck. Affixed to the chuck was a custom-made indicator for displaying the angular rotation of the second end of the sample when rotational torque was applied to the first end.

For each sample, the torque watch was rotated the desired number of degrees in the positive direction, held in the desired angular displacement position, and the torque reading in ounce-inches corresponding to that displacement read. The measurement was next repeated for angular displacement in the opposite negative direction for an angular displacement of the same magnitude. Measurements were obtained at angular displacements of plus and minus 30 degrees and plus and minus sixty degrees for each temporary lead tested. The torque watch used to obtain the data of Table 3 was a torque watch manufactured by Waters Manufacturing, Inc., where the watch had U.S. Design Pat. No. 177,889 displayed thereon.

TABLE 3

Transmitted Torque at Angular displacements of 30° and 60° for Selected Temporary Leads

| Lead Type | Angular Displacement (degrees) | Torque (oz.-in.) |
| --- | --- | --- |
| Present | +30 | 0.41 |
| Invention | −30 | 0.47 |
| (guide catheter | +60 | 0.81 |
| only) | −60 | 0.89 |
| Daig 5F | +30 | 0.09 |
| Lead | −30 | 0.08 |
| (lead body) | +60 | 0.20 |
|  | −60 | 0.19 |
| Elecath 5F | +30 | 0.04 |
| Lead | −30 | 0.04 |
| (II-KBE2) | +60 | 0.08 |
| (lead body) | −60 | 0.08 |
| TEMPTRON 4F | +30 | 0.04 |
| Lead | −30 | 0.03 |
| (lead body) | +60 | 0.06 |
|  | −60 | 0.05 |
| TEMPTRON 5F | +30 | 0.08 |
| Lead | −30 | 0.10 |
| (lead body) | +60 | 0.14 |
|  | −60 | 0.19 |

Table 3 and FIGS. 12 and 13 illustrate vividly the unexpectedly superior torque transmission characteristics of the present invention respecting prior art temporary leads. Table 3 and FIGS. 12 and 13 show that the guide catheter of the present invention transmits anywhere between four and ten times more torque between its proximal and distal ends than prior art temporary leads. Thus, the guide catheter of the present invention provides not only improved torque transmission in respect of prior art temporary leads, but provides torque transmission that is roughly an order of magnitude better than that attainable using prior art temporary leads only.

There are two preferred techniques for implanting the lead of the present invention. The first technique is referred to herein as the needle and sheath technique. The second technique is referred to herein as the dilator technique. Both techniques are well known to those of ordinary skill in the art.

In the first technique, a combined needle and sheath structure is used to locate the desired entry point vein. When the proper vein has been located, and after a syringe has been used to draw venous blood to confirm that the vein has indeed been perforated, the sheath is extended further into the vein, and the needle is withdrawn. Guide catheter 20 is then routed through the sheath into the vein, and guided to the desired intra-cardiac chamber and site, typically with the aid of a fluoroscope. Guide catheter 20 is positioned against the wall of the heart at the desired location, pulled away from the wall about one centimeter, and then lead body 15 is extended through guide catheter 20 until ring electrode 95 barely extends beyond end 210 of guide catheter 20; a fluoroscope is typically used to determine the relative positions of the distal tip of the guide catheter and the ring electrode.

Lead body 15 is then rotated clockwise for two to three revolutions to drive in and affix the helical coil to the endocardium and myocardium. Next, guide catheter 20 is withdrawn a further 2.5 centimeters from the wall, and gentle traction is applied to lead body 15 to ascertain whether sufficient mechanical affixation of the helical coil to the heart wall has occurred. If sufficient mechanical affixation is detected, lead body proximal end 35 is connected electrically and mechanically to a Pacing System Analyzer (PSA) or EPG to determine if appropriate sensing and pacing thresholds are provided by the lead. A patient cable may be disposed between lead body proximal end 35 and the PSA or EPG.

If sufficient mechanical affixation of the coil to the heart wall is not detected, guide catheter 20 is repositioned such that ring electrode 95 barely extends from the tip thereof, and lead body 15 is rotated counterclockwise to remove helical coil 80 from the heart wall. The process of affixing the coil to the heart wall is then repeated as described above.

After obtaining sufficient mechanical coupling of the coil to the heart wall, and after determining that an appropriate pacing threshold and suitable sensing are provided by the lead, lead body 15 is pushed through guide catheter 20 simultaneous with guide catheter 20 being withdrawn from the body. This procedure minimizes the traction or tension applied to lead body 15 and the heart wall. Once the distal tip of guide catheter 20 emerges from the body, lead body 15 is held against the wound site while guide catheter 20 is withdrawn over the proximal end of lead body 15. Strain relief of lead body 15 is typically effected using sutures, tape, gauze or the like. Finally, connectors 105 and 115 are connected to patient cables, a PSA, an EPG, or other diagnostic, support, or monitoring equipment.

The second dilator technique is broadly similar to the first technique except in respect of the differences outlined below. In the second technique, and as in the first technique, a combined needle and sheath structure is used to locate the desired entry point vein. When the proper vein has been located, and after a syringe has been used to draw venous blood to confirm that the vein has indeed been perforated, a guide wire is inserted through the needle and into the vein. The needle is removed, leaving the wire only in the vein. A second sheath or introducer having a hollow needle-shaped dilator disposed therewithin is next pushed over the guide wire and into the vein. First the guide wire is removed, followed by the removal of the dilator. The second sheath or introducer is left in the vein, and becomes the entry point for guide catheter 20.

Further details concerning implantation procedures are set forth a sales brochure entitled "MEDTRONIC™ TEMP- TRON™ Temporary Disposable Bipolar Leads" having a March, 1982 copyright notice, which is hereby incorporated by reference herein in its entirety.

The preceding specific embodiments are illustrative of the practice of the invention. It is to be understood, therefore, that other expedients known to those skilled in the art or disclosed herein, may be employed without departing from the invention or the scope of the appended claims. For example, the present invention is not limited to bipolar leads, unipolar leads or co-axial embodiments having three twisted inner wire conductors and sixteen braided outer wire conductors. Nor is the present invention limited to temporary pacing leads for bradycardia applications per se, but may find further application as a cardiac sensing lead only, a fetal monitoring and sensing lead, a defibrillating lead, a fluoroless lead, a balloon lead, or a lead for use in stent implantation or other surgical procedure where cardiac backup or pacing support is required. Additionally, the present invention is not limited in scope to temporary pacing leads having two electrodes and two electrical conductors only. Instead, it is contemplated that the present invention include within its scope temporary leads having more than two electrodes or conductors.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

The present invention further includes within its scope methods of implanting, using and making the leads described hereinabove. Many objects, features and advantages of the present invention also find application in the field of permanent pacing leads.

We claim:

1. A temporary active fixation endocardial pacing lead having distal and proximal ends, comprising:
   (a) a malleable, resilient lead body having a maximum diameter less than about 3.5 French and distal and proximal ends, the lead body comprising:
      (i) coaxial inner and outer electrical conductors, the outer conductor having an outer surface, electrically insulative material being disposed between the conductors, the inner conductor comprising at least one wire, the outer conductor comprising a plurality of wires capable of transferring sufficient torque from the proximal end of the lead body to the distal end of the lead body to permit screwable affixation of the distal end of the lead in endocardial tissue;
      (ii) an outer sheath formed of biocompatible and electrically insulative material, the sheath extending over and covering at least portions of the outer surface;
   (b) first and second electrical connectors attached, respectively, to the proximal ends of the inner and outer electrical conductors;
   (c) a helical screw-in retainer for active fixation in endocardial or myocardial tissue, the retainer being formed of biocompatible material, at least a portion of the retainer defining a tip electrode, the tip electrode being electrically and mechanically connected to the distal end of one of the inner and outer electrical conductors, the retainer having a diameter not exceeding about 4 French, the tip electrode having a surface area less than or equal to ten square millimeters;
   (d) a ring electrode disposed between the retainer and the distal end of the lead body, the ring electrode being formed of biocompatible material and electrically connected to the distal end of the electrical conductor not attached to the retainer, the ratio of the surface area of the ring electrode to the surface area of the tip electrode being greater than or equal to 2:1, and
   (e) a malleable, resilient tube-shaped guide catheter having a maximum outside diameter not exceeding about 6 French and formed of biocompatible material, the guide catheter having distal and proximal ends and inner and outer surfaces, the guide catheter sheathing and extending over at least a portion of the lead body, the inner surface of the guide catheter having a diameter sufficient to accept the lead body therewithin.

2. The endocardial lead of claim 1, wherein a ten-inch long sample of the guide catheter is capable of transmitting at least about 0.10 ounce-inches of torque between its proximal and distal ends when the proximal end is held in a fixed position and the distal end is rotated through an angular displacement of 30 degrees.

3. The endocardial lead of claim 1, wherein a ten-inch long sample of the guide catheter is capable of transmitting at least about 0.20 ounce-inches of torque between its proximal and distal ends when the proximal end is held in a fixed position and the distal end is rotated through an angular displacement of 30 degrees.

4. The endocardial lead of claim 1, wherein a ten-inch long sample of the guide catheter is capable of transmitting at least about 0.40 ounce-inches of torque between its proximal and distal ends when the proximal end is held in a fixed position and the distal end is rotated through an angular displacement of 30 degrees.

5. The endocardial lead of claim 1, wherein a ten-inch long sample of the guide catheter is capable of transmitting at least about 0.20 ounce-inches of torque between its proximal and distal ends when the proximal end is held in a fixed position and the distal end is rotated through an angular displacement of 60 degrees.

6. The endocardial lead of claim 1, wherein a ten-inch long sample of the guide catheter is capable of transmitting at least about 0.40 ounce-inches of torque between its proximal and distal ends when the proximal end is held in a fixed position and the distal end is rotated through an angular displacement of 60 degrees.

7. The endocardial lead of claim 1, wherein a ten-inch long sample of the guide catheter is capable of transmitting at least about 0.60 ounce-inches of torque between its proximal and distal ends when the proximal end is held in a fixed position and the distal end is rotated through an angular displacement of 60 degrees.

8. The endocardial lead of claim 1, wherein a ten-inch long sample of the guide catheter is capable of transmitting at least about 0.80 ounce-inches of torque between its proximal and distal ends when the proximal end is held in a fixed position and the distal end is rotated through an angular displacement of 60 degrees.

9. The endocardial lead of claim 1, further comprising a hub having distal and proximal ends, the first end being attached to the proximal end of the guide catheter, the hub having a bore extending between its distal and proximal ends, the bore having a diameter sufficient to slidingly accept the lead body therewithin.

10. The endocardial lead of claim 9, further comprising a hemostasis valve attached to the proximal end of the hub, the valve having a first bore disposed therewithin, the first bore having a diameter sufficient to slidingly accept the lead body therewithin.

11. The endocardial lead of claim 10, wherein the hemostasis valve further has a second bore disposed therewithin, the first end of the second bore being contiguous with and intersecting at least an oblique angle the first bore, the second end of the second bore terminating in a neck attached to and extending outwardly from the outer surface of the valve.

12. The endocardial lead of claim 11, wherein the neck receives a sealing cap on the outer end thereof.

13. The endocardial lead of claim 1, wherein the connectors are pin connectors.

14. The endocardial lead of claim 13, wherein the pin connectors are arranged in staggered offset fashion respecting the lead body.

15. The endocardial lead of claim 1, wherein the ratio of ring electrode surface area to tip electrode surface area is greater than or equal to about 2.5:1.

16. The endocardial lead of claim 1, wherein the ratio of ring electrode surface area to tip electrode surface area is greater than or equal to about 3:1.

17. The endocardial lead of claim 1, wherein the ratio of ring electrode surface area to tip electrode surface area is greater than or equal to about 3.5:1.

18. The endocardial lead of claim 1, wherein the ratio of ring electrode surface area to tip electrode surface area is greater than or equal to about 4:1.

19. The endocardial lead of claim 1, wherein the ratio of ring electrode surface area to tip electrode surface area is greater than or equal to about 4.5:1.

20. The endocardial lead of claim 1, wherein the ratio of ring electrode surface area to tip electrode surface area is greater than or equal to about 5:1.

21. The endocardial lead of claim 1, wherein the tip electrode has a surface area less than or equal to about 9 $mm^2$.

22. The endocardial lead of claim 1, wherein the tip electrode has a surface area less than or equal to about 8 $mm^2$.

23. The endocardial lead of claim 1, wherein the tip electrode has a surface area less than or equal to about 7 $mm^2$.

24. The endocardial lead of claim 1, wherein the tip electrode has a surface area less than or equal to about 5 $mm^2$.

25. The endocardial lead of claim 1, wherein the tip electrode has a surface area less than or equal to about 3 $mm^2$.

26. The endocardial lead of claim 1, wherein a ten-inch long sample of the guide catheter is capable of transmitting at least about 0.30 ounce-inches of torque between its proximal and distal ends when the proximal end is held in a fixed position and the distal end is rotated through an angular displacement of 30 degrees.

27. A temporary endocardial pacing lead having distal and proximal ends, comprising:
   (a) a malleable, resilient lead body having a maximum diameter less than about 3.5 French and distal and proximal ends, the lead body comprising:
      (i) coaxial inner and outer means for conducting electricity, the outer conducting means having an outer surface, electrically insulative material being disposed between the conducting means, the inner conducting means comprising at least one wire, the outer conducting means comprising a plurality of wires capable of transferring sufficient torque from the proximal end of the lead body to the distal end of the lead body to permit screwable affixation of the distal end of the lead in endocardial tissue;
      (ii) an outer sheathing means formed of biocompatible and electrically insulative material, the sheathing means extending over and covering at least portions of the outer surface;
   (b) first and second electrical connecting means attached, respectively, to the proximal ends of the inner and outer electrical conducting means;
   (c) active fixation means for active fixation in endocardial or myocardial tissue, the fixation means being formed of biocompatible material, at least a portion of the fixation means defining a tip electrode means, the tip electrode means being electrically and mechanically connected to the distal end of one of the inner and outer electrical conducting means, the fixation means having a diameter not exceeding about 4 French, the tip electrode having a surface area less than or equal to ten square millimeters;
   (d) a ring electrode means disposed between the fixation means and the distal end of the lead body, the ring electrode means being formed of biocompatible material and electrically connected to the distal end of the electrical conducting means not attached to the fixation means, the ratio of the surface area of the ring electrode means to the surface area of the tip electrode means being greater than or equal to 2:1, and
   (e) a malleable, resilient tube-shaped guide catheter means having a maximum outside diameter not exceeding about 6 French and formed of biocompatible material, the guide catheter means having distal and proximal ends and inner and outer surfaces, the guide catheter means sheathing and extending over at least a portion of the lead body, the inner surface of the guide catheter means having a diameter sufficient to accept the lead body therewithin.

28. The endocardial lead of claim 27, further comprising a hub means having distal and proximal ends, the first end being attached to the proximal end of the guide catheter means, the hub means having a bore extending between its distal and proximal ends, the bore having a diameter sufficient to slidingly accept the lead body therewithin.

29. The endocardial lead of claim 28, further comprising a hemostasis valve means attached to the proximal end of the hub means, the valve means having a first bore disposed therewithin, the first bore having a diameter sufficient to slidingly accept the lead body therewithin.

30. The endocardial lead of claim 29, wherein the hemostasis valve means further has a second bore disposed therewithin, the first end of the second bore being contiguous with and intersecting at least an oblique angle the first bore, the second end of the second bore terminating in a neck attached to and extending outwardly from the outer surface of the valve means.

31. The endocardial lead of claim 30, wherein the neck receives a sealing cap means on the outer end thereof.

32. The endocardial lead of claim 27, wherein the connectors are pin connectors.

33. The endocardial lead of claim 32, wherein the pin connectors are arranged in staggered offset fashion respecting the lead body.

34. The endocardial lead of claim 27, wherein a ten-inch long sample of the guide catheter is capable of transmitting at least about 0.10 ounce-inches of torque between its proximal and distal ends when the proximal end is held in a fixed position and the distal end is rotated through an angular displacement of 30 degrees.

35. The endocardial lead of claim 27, wherein a ten-inch long sample of the guide catheter is capable of transmitting at least about 0.20 ounce-inches of torque between its proximal and distal ends when the proximal end is held in a fixed position and the distal end is rotated through an angular displacement of 30 degrees.

36. The endocardial lead of claim 27, wherein a ten-inch long sample of the guide catheter is capable of transmitting at least about 0.30 ounce-inches of torque between its proximal and distal ends when the proximal end is held in a fixed position and the distal end is rotated through an angular displacement of 30 degrees.

37. The endocardial lead of claim 27, wherein a ten-inch long sample of the guide catheter is capable of transmitting at least about 0.40 ounce-inches of torque between its proximal and distal ends when the proximal end is held in a fixed position and the distal end is rotated through an angular displacement of 30 degrees.

38. The endocardial lead of claim 27, wherein a ten-inch long sample of the guide catheter is capable of transmitting at least about 0.20 ounce-inches of torque between its proximal and distal ends when the proximal end is held in a fixed position and the distal end is rotated through an angular displacement of 60 degrees.

39. The endocardial lead of claim 27, wherein a ten-inch long sample of the guide catheter is capable of transmitting at least about 0.40 ounce-inches of torque between its proximal and distal ends when the proximal end is held in a fixed position and the distal end is rotated through an angular displacement of 60 degrees.

40. The endocardial lead of claim 27, wherein a ten-inch long sample of the guide catheter is capable of transmitting at least about 0.60 ounce-inches of torque between its proximal and distal ends when the proximal end is held in a fixed position and the distal end is rotated through an angular displacement of 60 degrees.

41. The endocardial lead of claim 27, wherein a ten-inch long sample of the guide catheter is capable of transmitting at least about 0.80 ounce-inches of torque between its proximal and distal ends when the proximal end is held in a fixed position and the distal end is rotated through an angular displacement of 60 degrees.

42. The endocardial lead of claim 27, wherein the ratio of ring electrode surface area to tip electrode surface area is greater than or equal to about 2.5:1.

43. The endocardial lead of claim 27, wherein the ratio of ring electrode surface area to tip electrode surface area is greater than or equal to about 3:1.

44. The endocardial lead of claim 27, wherein the ratio of ring electrode surface area to tip electrode surface area is greater than or equal to about 3.5:1.

45. The endocardial lead of claim 27, wherein the ratio of ring electrode surface area to tip electrode surface area is greater than or equal to about 4.5:1.

46. The endocardial lead of claim 27, wherein the ratio of ring electrode surface area to tip electrode surface area is greater than or equal to about 5:1.

47. The endocardial lead of claim 27, wherein the tip electrode has a surface area less than or equal to about 9 $mm^2$.

48. The endocardial lead of claim 27, wherein the tip electrode has a surface area less than or equal to about 8 $mm^2$.

49. The endocardial lead of claim 27, wherein the tip electrode has a surface area less than or equal to about 7 $mm^2$.

50. The endocardial lead of claim 27, wherein the tip electrode has a surface area less than or equal to about 5 $mm^2$.

51. The endocardial lead of claim 27, wherein the tip electrode has a surface area less than or equal to about 3 $mm^2$.

52. The endocardial lead of claim 27, wherein the ratio of ring electrode surface area to tip electrode surface area is greater than or equal to about 4:1.

53. A temporary active fixation endocardial pacing lead having distal and proximal ends, comprising:

(a) a malleable, resilient lead body having an outer surface defining a maximum diameter less than about 3.5 French, the lead body comprising distal and proximal ends, an outer sheath, and first and second electrical conductors, electrically insulative material being disposed between the conductors, the outer sheath formed of biocompatible and electrically insulative material, the sheath extending over and covering at least portions of the outer surface;

(b) first and second electrical connectors attached, respectively, to the proximal ends of the first and second electrical conductors;

(c) an active fixation device for active fixation in endocardial or myocardial tissue, the active fixation device being formed of biocompatible material, at least a portion of the active fixation device defining a tip electrode, the tip electrode being electrically and mechanically connected to the distal end of one of the first and second electrical conductors, the active fixation device having a diameter not exceeding about 4 French, the tip electrode having a surface area less than or equal to ten square millimeters;

(d) a ring electrode disposed between the active fixation device and the distal end of the lead body, the ring electrode being formed of biocompatible material and electrically connected to the distal end of the electrical conductor not attached to the active fixation device, the ratio of the surface area of the ring electrode to the surface area of the tip electrode being greater than or equal to 2:1, and (e) a malleable, resilient tube-shaped guide catheter having a maximum outside diameter not exceeding about 6 French and formed of biocompatible material, the guide catheter having distal and proximal ends and inner and outer surfaces, the guide catheter sheathing and extending over at least a portion of the lead body, the inner surface of the guide catheter having a diameter sufficient to accept the lead body therewithin.

54. The endocardial lead of claim 53, further comprising a hub means having distal and proximal ends, the first end being attached to the proximal end of the guide catheter means, the hub means having a bore extending between its distal and proximal ends, the bore having a diameter sufficient to slidingly accept the lead body therewithin.

55. The endocardial lead of claim 54, further comprising a hemostasis valve means attached to the proximal end of the hub means, the valve means having a first bore disposed therewithin, the first bore having a diameter sufficient to slidingly accept the lead body therewithin.

56. The endocardial lead of claim 55, wherein the hemostasis valve means further has a second bore disposed therewithin, the first end of the second bore being contiguous with and intersecting at least an oblique angle the first bore, the second end of the second bore terminating in a neck attached to and extending outwardly from the outer surface of the valve means.

57. The endocardial lead of claim 56, wherein the neck receives a sealing cap means on the outer end thereof.

58. The endocardial lead of claim 53, wherein the connectors are pin connectors.

59. The endocardial lead of claim 58, wherein the pin connectors are arranged in staggered offset fashion respecting the lead body.

60. The endocardial lead of claim 53, wherein a ten-inch long sample of the guide catheter is capable of transmitting at least about 0.10 ounce-inches of torque between its proximal and distal ends when the proximal end is held in a fixed position and the distal end is rotated through an angular displacement of 30 degrees.

61. The endocardial lead of claim 53, wherein a ten-inch long sample of the guide catheter is capable of transmitting at least about 0.20 ounce-inches of torque between its proximal and distal ends when the proximal end is held in a fixed position and the distal end is rotated through an angular displacement of 30 degrees.

62. The endocardial lead of claim 53, wherein a ten-inch long sample of the guide catheter is capable of transmitting at least about 0.30 ounce-inches of torque between its proximal and distal ends when the proximal end is held in a fixed position and the distal end is rotated through an angular displacement of 30 degrees.

63. The endocardial lead of claim 53, wherein a ten-inch long sample of the guide catheter is capable of transmitting at least about 0.40 ounce-inches of torque between its proximal and distal ends when the proximal end is held in a fixed position and the distal end is rotated through an angular displacement of 30 degrees.

64. The endocardial lead of claim 53, wherein a ten-inch long sample of the guide catheter is capable of transmitting at least about 0.20 ounce-inches of torque between its proximal and distal ends when the proximal end is held in a fixed position and the distal end is rotated through an angular displacement of 60 degrees.

65. The endocardial lead of claim 53, wherein a ten-inch long sample of the guide catheter is capable of transmitting at least about 0.40 ounce-inches of torque between its proximal and distal ends when the proximal end is held in a fixed position and the distal end is rotated through an angular displacement of 60 degrees.

66. The endocardial lead of claim 53, wherein a ten-inch long sample of the guide catheter is capable of transmitting at least about 0.60 ounce-inches of torque between its proximal and distal ends when the proximal end is held in a fixed position and the distal end is rotated through an angular displacement of 60 degrees.

67. The endocardial lead of claim 53, wherein a ten-inch long sample of the guide catheter is capable of transmitting at least about 0.80 ounce-inches of torque between its proximal and distal ends when the proximal end is held in a fixed position and the distal end is rotated through an angular displacement of 60 degrees.

68. The endocardial lead of claim 53, wherein the ratio of ring electrode surface area to tip electrode surface area is greater than or equal to about 2.5:1.

69. The endocardial lead of claim 53, wherein the ratio of ring electrode surface area to tip electrode surface area is greater than or equal to about 3:1.

70. The endocardial lead of claim 53, wherein the ratio of ring electrode surface area to tip electrode surface area is greater than or equal to about 3.5:1.

71. The endocardial lead of claim 53, wherein the ratio of ring electrode surface area to tip electrode surface area is greater than or equal to about 4:1.

72. The endocardial lead of claim 53, wherein the ratio of ring electrode surface area to tip electrode surface area is greater than or equal to about 4.5:1.

73. The endocardial lead of claim 53, wherein the ratio of ring electrode surface area to tip electrode surface area is greater than or equal to about 5:1.

74. The endocardial lead of claim 53, wherein the tip electrode has a surface area less than or equal to about 9 $mm^2$.

75. The endocardial lead of claim 53, wherein the tip electrode has a surface area less than or equal to about 8 $mm^2$.

76. The endocardial lead of claim 53, wherein the tip electrode has a surface area less than or equal to about 7 $mm^2$.

77. The endocardial lead of claim 53, wherein the tip electrode has a surface area less than or equal to about 5 $mm^2$.

78. The endocardial lead of claim 53, wherein the tip electrode has a surface area less than or equal to about 3 $mm^2$.

79. A temporary active fixation endocardial pacing lead having distal and proximal ends, comprising:

(a) a malleable, resilient lead body means having an outer surface defining a maximum diameter less than about 3.5 French, the lead body means comprising distal and proximal ends, an outer sheath, and first and second electrical conducting means, means for electrically insulating being disposed between the conducting means, the outer sheath formed of biocompatible and electrically insulative material, the sheath extending over and covering at least portions of the outer surface;

(b) first and second electrical connecting means attached, respectively, to the proximal ends of the first and second electrical conducting means;

(c) means for actively affixing to endocardial or myocardial tissue, the active fixation means being formed of biocompatible material, at least a portion of the active fixation means defining a tip electrode means, the tip electrode means being electrically and mechanically connected to the distal end of one of the first and second electrical conducting, the active fixation means having a diameter not exceeding about 4 French, the tip electrode means having a surface area less than or equal to ten square millimeters;

(d) a ring electrode means disposed between the active fixation means and the distal end of the lead body means, the ring electrode means being formed of biocompatible material and electrically connected to the distal end of the electrical conducting means not attached to the active fixation means, the ratio of the surface area of the ring electrode means to the surface area of the tip electrode means being greater than or equal to 2:1, and (e) a malleable, resilient tube-shaped guide catheter means having a maximum outside diameter not exceeding about 6 French and formed of biocompatible material, the guide catheter means having distal and proximal ends and inner and outer surfaces, the guide catheter means sheathing and extending over at least a portion of the lead body means, the inner surface of the guide catheter means having a diameter sufficient to accept the lead body means therewithin.

80. The endocardial lead of claim 79, further comprising a hub means having distal and proximal ends, the first end being attached to the proximal end of the guide catheter means, the hub means having a bore extending between its distal and proximal ends, the bore having a diameter sufficient to slidingly accept the lead body therewithin.

81. The endocardial lead of claim 80, further comprising a hemostasis valve means attached to the proximal end of the hub means, the valve means having a first bore disposed therewithin, the first bore having a diameter sufficient to slidingly accept the lead body means therewithin.

82. The endocardial lead of claim 81, wherein the hemostasis valve means further has a second bore disposed therewithin, the first end of the second bore being contiguous with and intersecting at least an oblique angle the first bore, the second end of the second bore terminating in a neck attached to and extending outwardly from the outer surface of the valve means.

83. The endocardial lead of claim 82, wherein the neck receives a sealing cap means on the outer end thereof.

84. The endocardial lead of claim 79, wherein the connectors are pin connectors.

85. The endocardial lead of claim 84, wherein the pin connectors are arranged in staggered offset fashion respecting the lead body.

86. The endocardial lead of claim 79, wherein a ten-inch long sample of the guide catheter is capable of transmitting at least about 0.10 ounce-inches of torque between its proximal and distal ends when the proximal end is held in a fixed position and the distal end is rotated through an angular displacement of 30 degrees.

87. The endocardial lead of claim 79, wherein a ten-inch long sample of the guide catheter is capable of transmitting at least about 0.20 ounce-inches of torque between its proximal and distal ends when the proximal end is held in a fixed position and the distal end is rotated through an angular displacement of 30 degrees.

88. The endocardial lead of claim 79, wherein a ten-inch long sample of the guide catheter is capable of transmitting at least about 0.30 ounce-inches of torque between its proximal and distal ends when the proximal end is held in a fixed position and the distal end is rotated through an angular displacement of 30 degrees.

89. The endocardial lead of claim 79, wherein a ten-inch long sample of the guide catheter is capable of transmitting at least about 0.40 ounce-inches of torque between its proximal and distal ends when the proximal end is held in a fixed position and the distal end is rotated through an angular displacement of 30 degrees.

90. The endocardial lead of claim 79, wherein a ten-inch long sample of the guide catheter is capable of transmitting at least about 0.20 ounce-inches of torque between its proximal and distal ends when the proximal end is held in a fixed position and the distal end is rotated through an angular displacement of 60 degrees.

91. The endocardial lead of claim 79, wherein a ten-inch long sample of the guide catheter is capable of transmitting at least about 0.40 ounce-inches of torque between its proximal and distal ends when the proximal end is held in a fixed position and the distal end is rotated through an angular displacement of 60 degrees.

92. The endocardial lead of claim 79, wherein a ten-inch long sample of the guide catheter is capable of transmitting at least about 0.60 ounce-inches of torque between its proximal and distal ends when the proximal end is held in a fixed position and the distal end is rotated through an angular displacement of 60 degrees.

93. The endocardial lead of claim 79, wherein a ten-inch long sample of the guide catheter is capable of transmitting at least about 0.80 ounce-inches of torque between its proximal and distal ends when the proximal end is held in a fixed position and the distal end is rotated through an angular displacement of 60 degrees.

94. The endocardial lead of claim 79, wherein the ratio of ring electrode surface area to tip electrode surface area is greater than or equal to about 2.5:1.

95. The endocardial lead of claim 79, wherein the ratio of ring electrode surface area to tip electrode surface area is greater than or equal to about 3:1.

96. The endocardial lead of claim 79, wherein the ratio of ring electrode surface area to tip electrode surface area is greater than or equal to about 3.5:1.

97. The endocardial lead of claim 79, wherein the ratio of ring electrode surface area to tip electrode surface area is greater than or equal to about 4:1.

98. The endocardial lead of claim 79, wherein the ratio of ring electrode surface area to tip electrode surface area is greater than or equal to about 4.5:1.

99. The endocardial lead of claim 79, wherein the ratio of ring electrode surface area to tip electrode surface area is greater than or equal to about 5:1.

100. The endocardial lead of claim 79, wherein the tip electrode has a surface area less than or equal to about 9 $mm^2$.

101. The endocardial lead of claim 79, wherein the tip electrode has a surface area less than or equal to about 8 $mm^2$.

102. The endocardial lead of claim 79, wherein the tip electrode has a surface area less than or equal to about 7 $mm^2$.

103. The endocardial lead of claim 79, wherein the tip electrode has a surface area less than or equal to about 5 $mm^2$.

104. The endocardial lead of claim 79, wherein the tip electrode has a surface area less than or equal to about 3 $mm^2$.

105. A temporary lead system, comprising:
(a) a lead body having proximal and distal ends, the outer diameter of the lead body not exceeding about 3.5 French, the lead body comprising at least first and second electrical conductors separated by electrically insulative material, a tip electrode disposed near the distal end of the lead body, a ring electrode disposed proximally of the tip electrode, and an active fixation device mechanically and electrically attached to the tip electrode, the tip electrode having a surface area less than or equal to ten square millimeters, the ratio of the surface area of the ring electrode to the surface area of the tip electrode exceeding about 2:1, the tip electrode being mechanically and electrically connected to the first conductor, the ring electrode being mechanically and electrically connected to the second conductor, the lead body having first and second electrical connectors disposed at its proximal end, the first and second electrical connectors being mechanically and electrically connected to the first and second electrical conductors, respectively, and
(b) a guide catheter forming a resilient tube shape, having a maximum outside diameter not exceeding about 6 French and formed of biocompatible material, the guide catheter having distal and proximal ends and inner and outer surfaces, the guide catheter sheathing and extending over at least a portion of the lead body, the inner surface of the guide catheter having a diameter sufficient to accept the lead body therewithin,
wherein a ten-inch long sample of the guide catheter is capable off transmitting at least about 0.10 ounce-inches of torque between its proximal and distal ends when the proximal end is held in a fixed position and the distal end is rotated through an angular displacement of 30 degrees.

106. The endocardial lead of claim 105, wherein a ten-inch long sample of the guide catheter is capable of transmitting at least about 0.20 ounce-inches of torque between its proximal and distal ends when the proximal end is held in a fixed position and the distal end is rotated through an angular displacement of 30 degrees.

107. The endocardial lead of claim 105, wherein a ten-inch long sample of the guide catheter is capable of transmitting at least about 0.30 ounce-inches of torque between its proximal and distal ends when the proximal end is held in a fixed position and the distal end is rotated through an angular displacement of 30 degrees.

108. The endocardial lead of claim 105, wherein a ten-inch long sample of the guide catheter is capable of transmitting at least about 0.40 ounce-inches of torque between its proximal and distal ends when the proximal end is held in a fixed position and the distal end is rotated through an angular displacement of 30 degrees.

109. The endocardial lead of claim 105, wherein a ten-inch long sample of the guide catheter is capable of transmitting at least about 0.20 ounce-inches of torque between its proximal and distal ends when the proximal end is held in a fixed position and the distal end is rotated through an angular displacement of 60 degrees.

110. The endocardial lead of claim 105, wherein a ten-inch long sample of the guide catheter is capable of transmitting at least about 0.40 ounce-inches of torque between its proximal and distal ends when the proximal end is held in a fixed position and the distal end is rotated through an angular displacement of 60 degrees.

111. The endocardial lead of claim 105, wherein a ten-inch long sample of the guide catheter is capable of transmitting at least about 0.60 ounce-inches of torque between its proximal and distal ends when the proximal end is held in a fixed position and the distal end is rotated through an angular displacement of 60 degrees.

112. The endocardial lead of claim 105, wherein a ten-inch long sample of the guide catheter is capable of transmitting at least about 0.80 ounce-inches of torque between its proximal and distal ends when the proximal end is held in a fixed position and the distal end is rotated through an angular displacement of 60 degrees.

113. The endocardial lead of claim 105, wherein the ratio of ring electrode surface area to tip electrode surface area is greater than or equal to about 2.5:1.

114. The endocardial lead of claim 105, wherein the ratio of ring electrode surface area to tip electrode surface area is greater than or equal to about 3:1.

115. The endocardial lead of claim 105, wherein the ratio of ring electrode surface area to tip electrode surface area is greater than or equal to about 3.5:1.

116. The endocardial lead of claim 105, wherein the ratio of ring electrode surface area to tip electrode surface area is greater than or equal to about 4:1.

117. The endocardial lead of claim 105, wherein the ratio of ring electrode surface area to tip electrode surface area is greater than or equal to about 4.5:1.

118. The endocardial lead of claim 105, wherein the ratio of ring electrode surface area to tip electrode surface area is greater than or equal to about 5:1.

119. The endocardial lead of claim 105, wherein the tip electrode has a surface area less than or equal to about 9 $mm^2$.

120. The endocardial lead of claim 105, wherein the tip electrode has a surface area less than or equal to about 8 $mm^2$.

121. The endocardial lead of claim 105, wherein the tip electrode has a surface area less than or equal to about 7 $mm^2$.

122. The endocardial lead of claim 105, wherein the tip electrode has a surface area less than or equal to about 5 $mm^2$.

123. A method of making a temporary active fixation endocardial pacing lead having distal and proximal ends, comprising the steps of:

(a) providing a malleable, resilient lead body having an outer surface defining a maximum diameter less than about 3.5 French, the lead body comprising distal and proximal ends, an outer sheath, and first and second electrical conductors, electrically insulative material being disposed between the conductors, the outer sheath formed of biocompatible and electrically insulative material, the sheath extending over and covering at least portions of the outer surface;

(b) providing first and second electrical connectors attached, respectively, to the proximal ends of the first and second electrical conductors;

(c) providing an active fixation device for active fixation in endocardial or myocardial tissue, the active fixation device being formed of biocompatible material, at least a portion of the active fixation device defining a tip electrode, the tip electrode being electrically and mechanically connected to the distal end of one of the first and second electrical conductors, the active fixation device having a diameter not exceeding about 4 French, the tip electrode having a surface area less than or equal to ten square millimeters;

(d) providing a ring electrode disposed between the active fixation device and the distal end of the lead body, the ring electrode being formed of biocompatible material and electrically connected to the distal end of the electrical conductor not attached to the active fixation device, the ratio of the surface area of the ring electrode to the surface area of the tip electrode being greater than or equal to 2:1, and (e) providing a malleable, resilient tube-shaped guide catheter having a maximum outside diameter not exceeding about 6 French and formed of biocompatible material, the guide catheter having distal and proximal ends and inner and outer surfaces, the guide catheter sheathing and extending over at least a portion of the lead body, the inner surface of the guide catheter having a diameter sufficient to accept the lead body therewithin.

\* \* \* \* \*